United States Patent
Yokoyama et al.

(10) Patent No.: US 8,153,277 B2
(45) Date of Patent: Apr. 10, 2012

(54) COMPOUND HAVING THIADIAZOLE RING STRUCTURE SUBSTITUTED WITH PYRIDYL GROUP AND ORGANIC ELECTROLUMINESCENT DEVICE

(75) Inventors: Norimasa Yokoyama, Ibaraki (JP); Toru Akisada, Yamaguchi (JP); Shigeru Kusano, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 266 days.

(21) Appl. No.: 12/294,323

(22) PCT Filed: Mar. 20, 2007

(86) PCT No.: PCT/JP2007/055752
§ 371 (c)(1),
(2), (4) Date: Sep. 24, 2008

(87) PCT Pub. No.: WO2007/119461
PCT Pub. Date: Oct. 25, 2007

(65) Prior Publication Data
US 2009/0108750 A1 Apr. 30, 2009

(30) Foreign Application Priority Data
Mar. 24, 2006 (JP) ................ 2006-082969

(51) Int. Cl.
*H01L 51/54* (2006.01)
*C07D 417/14* (2006.01)
*C09K 11/06* (2006.01)

(52) U.S. Cl. ......... 428/690; 428/917; 313/504; 546/256

(58) Field of Classification Search .......... None
See application file for complete search history.

(56) References Cited

U.S. PATENT DOCUMENTS

| | | | | |
|---|---|---|---|---|
| 5,076,961 A * | 12/1991 | Nakamura et al. | ....... | 252/299.61 |
| 5,336,546 A * | 8/1994 | Hironaka et al. | ....... | 428/209 |
| 2008/0017846 A1* | 1/2008 | Miki et al. | ....... | 257/40 |
| 2009/0134780 A1* | 5/2009 | Ono et al. | ....... | 313/504 |

FOREIGN PATENT DOCUMENTS

| | | |
|---|---|---|
| JP | 3-43488 | 2/1991 |
| JP | 3-83971 | 4/1991 |
| JP | 3-178971 | 8/1991 |
| JP | 4-13797 | 1/1992 |
| JP | 4-28787 | 1/1992 |
| JP | 4-272989 | 9/1992 |
| JP | 8-48656 | 2/1996 |
| JP | 2721442 | 11/1997 |
| JP | 2734341 | 1/1998 |
| JP | 2000-505822 | 5/2000 |
| JP | 3194657 | 6/2001 |
| JP | 3316236 | 6/2002 |
| JP | 3486994 | 10/2003 |
| JP | 2004-217549 | 8/2004 |
| WO | WO 2005092888 A1 * | 10/2005 |
| WO | WO 2007029696 A1 * | 3/2007 |

OTHER PUBLICATIONS

Chambers et al. J. Chem. Soc. (C) 1968, 1933-1937. Year of publication: 1968.*
Chishio Hosokawa, et al., Preprints for 9$^{th}$ Workshop of Japan Applied Physics, 2001, pp. 55-61.
Takeo Wakimoto, "Optimization of driving lifetime durability in organic LED devices using phosphorescent guest emitter", Preprints for 9$^{th}$ Workshop of Japan Applied Physics, 2001, pp. 23-31.
Chihaya Adachi, et al., "Electroluminescence in Organic Films with Three-Layer Structure", Japanese Journal of Applied Physics, vol. 27, No. 2, Feb. 1988, pp. L269-L271.
P. B. Rasmussen, et al., "Studies on organophosphorus compounds XLIX. An improved method for the preparation of 2,5-disbstituted 1,3,4-thiadiazoles and 1,3,4-thiadiazole-2(3H)-thiones", Bull. Soc. Chim. France, 1985, pp. II-62-II-65.
K. Dimitrowa, et al., "Biphenyl- und terphenylanaloge 1,3,4-Thiadiazole", Journal f. prakt. Chemie. Band, 322, Heft 6, 1980, pp. 933-944.
R. D. Chambers, et al., "Polyfluoroheterocyclic compounds. Part XIV. Some reactions of Tetrafluoroisonicotinic Acid and Pentafluorobenzoic Acid", Journal of the Chemical Society, vol. 15, 1968, pp. 1933-1937 and 1 front page.

* cited by examiner

*Primary Examiner* — Lynda Salvatore
*Assistant Examiner* — Andrew K Bohaty
(74) *Attorney, Agent, or Firm* — Oblon, Spivak, McClelland, Maier & Neustadt, L.L.P.

(57) ABSTRACT

An object of the present invention is to provide an organic compound having excellent characteristics, which is excellent in electron injection/transport performance, has hole blocking property and is high in stability in a thin film state, as a material for an organic EL device having high efficiency and high durability, and further to provide an organic EL device having high efficiency and high durability using this compound. The invention relates to a compound represented by general formula (1), which has a thiadiazole ring structure substituted with a substituted pyridyl group, and to an organic EL device having a pair of electrodes and at least one organic layer interposed therebetween, wherein the compound is contained as a constituent material of at least one of the organic layer(s).

[Chem. 1]

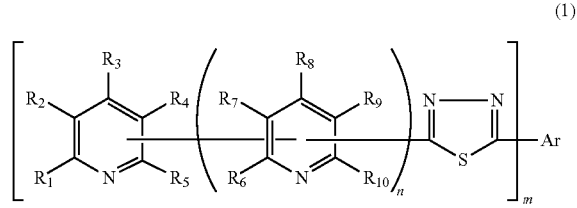

(1)

14 Claims, 5 Drawing Sheets

COMPOUND HAVING THIADIAZOLE RING STRUCTURE SUBSTITUTED WITH PYRIDYL GROUP AND ORGANIC ELECTROLUMINESCENT DEVICE

TECHNICAL FIELD

The present invention relates to a compound suitable for an organic electroluminescent (EL) device which is a self-luminescent device suitable for various display systems, and also relates to a device. Particularly, the present invention relates to a compound having a thiadiazole ring structure substituted with a substituted pyridyl group and to an organic EL device using the compound.

BACKGROUND ART

Since the organic EL devices are self-luminescent devices, they are bright, excellent in visibility, and capable of giving clear display as compared to liquid crystal devices, and studies thereon have actively been conducted.

In 1987, C. W. Tang et al. of Eastman Kodak Co. have turned the organic EL device using an organic material into practical utilization by developing a multilayer structure device wherein various functions are respectively distributed to materials. They laminated a fluorescent material capable of transporting electrons and an organic substance capable of transporting holes, and injected both of the charges into the fluorescent material layer to emit a light, thereby achieving a high luminance of 1,000 cd/m² or more at a voltage of 10 V or less (see patent document 1 and patent document 2, for example).

Patent Document 1: JP-A-8-48656
Patent Document 2: Japanese Patent No. 3,194,657

Many improvements have hitherto been made for practical application of the organic EL devices, and high efficiency and durability are achieved by an electroluminescence device in which various roles are further subdivided and in which an anode, a hole injection layer, a hole transport layer, an emitting layer, an electron transport layer, an electron injection layer and a cathode are provided in this order on a substrate (for example, see non-patent document 1).

Non-Patent Document 1: Preprints for 9th Workshop of Japan Applied Physics, pages 55 to 61, (2001)

In addition, for the purpose of further improving luminous efficiency, there has been an attempt of utilizing a triplet exciton, and the utilization of phosphorescence-emitting substance has been studied (for example, see non-patent document 2).

Non-Patent Document 2: Preprints for 9th Workshop of Japan Applied Physics, pages 23 to 31, (2001)

The emitting layer may be prepared by doping a charge transporting compound generally called a host material, with a fluorescent substance or a phosphorescence-emitting substance. As described in the above-mentioned workshop preprints, selection of an organic material in the organic EL device has a great influence on various characteristics such as efficiency and durability of the device.

In organic EL devices, charges injected from both electrodes recombine in the emitting layer to thereby provide light emission. However, the mobility of holes is higher than the electron mobility, so that a reduction in efficiency caused by that holes partially pass through the emitting layer becomes a problem. For this reason, an electron transport material having a high electron mobility has been demanded.

Tris(8-hydroxyquinoline) aluminum (hereinafter referred to as Alq3 for brevity), a typical light-emitting material, is generally used as an electron transport material, but the electron mobility thereof is considered to be low. For this reason, 2-(4-biphenylyl)-5-(4-t-butylphenyl)-1,3,4-oxadiazole (hereinafter referred to as PBD for brevity) and the like have been proposed as materials having a high mobility (for example, see non-patent document 3).

Non-Patent Document 3: Jpn. J. Appl. Phys., 27, L269 (1988)

However, it is pointed out that PBD is poor in stability in a thin film state, such as easy occurrence of crystallization, and various oxadiazole derivatives have been proposed (for example, see patent documents 3 to 5).

Patent Document 3: Japanese Patent No. 2,721,442
Patent Document 4: Japanese Patent No. 3,316,236
Patent Document 5: Japanese Patent No. 3,486,994

These electron transport materials have been improved in stability compared with PBD, but the improvement is not considered yet to be sufficient. From the viewpoint of the balance with the hole mobility, the electron mobility is still insufficient. For these reasons, Alq3 having good stability has been used as the electron transport material in many cases. However, satisfactory device characteristics have not been obtained.

Further, as a measure for preventing holes from partially passing through the emitting layer to thereby improve the probability of charge recombination in the emitting layer, there is a method of inserting a hole blocking layer. As hole blocking materials, there have hitherto been proposed a triazole derivative (for example, see patent document 6), bathocuproine (hereinafter referred to as BCP for brevity), a mixed-ligand complex of aluminum (BAlq) (for example, see non-patent document 2) and the like.

Patent Document 6: Japanese Patent No. 2,734,341

However, these materials are each lacking in film stability, or insufficient in the function of blocking holes. The hole blocking material which has been generally used at present is BCP. However, this compound is not considered to be a sufficiently stable material, so that it is not considered to sufficiently function as the hole blocking layer. Thus, satisfactory device characteristics have not been obtained.

In order to improve the device characteristics of organic EL devices, an organic compound excellent in electron injection/transport performance and in hole blocking property and high in stability in a thin film state has been demanded.

DISCLOSURE OF THE INVENTION

Problems to be Solved by the Invention

An object of the invention is to provide an organic compound having excellent characteristics, which is excellent in electron injection/transport performance, has hole blocking property and is high in stability in a thin film state, as a material for an organic EL device having high efficiency and high durability, and further to provide an organic EL device having high efficiency and high durability using the compound. Physical characteristics of the organic compound suitable for the invention include (1) good electron injection properties, (2) high electron mobility, (3) excellent hole blocking property, (4) stable thin film state and (5) excellent heat resistance. Further, physical characteristics of the device suitable for the invention include (1) high luminous efficiency, (2) low light emission initiating voltage, (3) low practical driving voltage and (4) high maximum light emission luminance.

Means for Solving the Problems

Then, in order to achieve the above-mentioned objects, the present inventors have designed a novel organic compound in which a substituted pyridine ring is connected to a thiadiazole ring, which is the ring where the oxygen atom of an oxadiazole ring is replaced with a sulfur atom, paying attention to that nitrogen atom of a pyridine ring with high electron affinity has an ability of coordination with a metal, and is excellent heat resistance. Using the compound, the present inventors have experimentally produced various organic EL devices, and have made intensive characteristic evaluations of the devices, thereby resulting in completion of the invention.

That is, the invention provides a compound represented by general formula (1), which has a thiadiazole ring structure substituted with a substituted pyridyl group, and also provides an organic EL device comprising a pair of electrodes and at least one organic layer interposed therebetween, wherein at least one organic layer contains, as a constituent material thereof, the compound.

[Chem. 1]

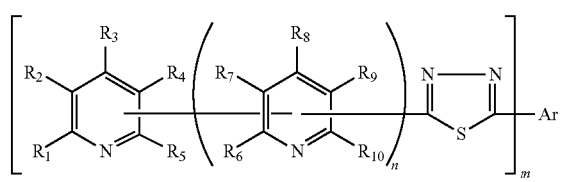

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a fluorine atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded.

The aromatic hydrocarbon group, the aromatic heterocyclic group and the condensed polycyclic aromatic group in the substituted or unsubstituted aromatic hydrocarbon group, the substituted or unsubstituted aromatic heterocyclic group and the substituted or unsubstituted condensed polycyclic aromatic group represented by Ar of general formula (1) specifically include a phenyl group, a biphenyl group, a terphenyl group, a tetrakisphenyl group, a styryl group, a naphthyl group, an anthryl group, an acenaphthenyl group, a fluorenyl group, a phenantolyl group, an indenyl group, a pyrenyl group, a pyridyl group, a pirimidyl group, a furanyl group, a pyronyl group, a thiophenyl group, a quinolyl group, a benzofuranyl group, a benzothiophenyl group, an indolyl group, a carbazolyl group, a benzoxazolyl group, a quinoxalyl group, a benzimidazolyl group, a pyrazolyl group, a dibenzofuranyl group, a dibenzothiophenyl group and a naphthylidinyl group.

The substituent group in the substituted aromatic hydrocarbon group, the substituted aromatic heterocyclic group and the substituted condensed polycyclic aromatic group represented by Ar of general formula (1) specifically include a fluorine atom, a chlorine atom, a cyano group, a hydroxyl group, a nitro group, an alkyl group, an alkoxy group, an amino group, a substituted amino group, a trifluoromethyl group, a phenyl group, a tolyl group, a naphthyl group and an aralkyl group.

The aromatic hydrocarbon group in the substituted or unsubstituted aromatic hydrocarbon group represented by R1 to R10 of general formula (1) specifically include a phenyl group, a biphenyl group, a terphenyl group, a tetrakisphenyl group, a styryl group, a naphthyl group, a fluorenyl group, a phenantolyl group, an indenyl group and a pyrenyl group.

The substituent group in the substituted aromatic hydrocarbon group represented by R1 to R10 in general formula (1) specifically include a fluorine atom, a chlorine atom, a trifluoromethyl group and an alkyl group having 1 to 6 carbon atoms.

The compound represented by general formula (1) of the invention, which has a thiadiazole ring structure substituted with a substituted pyridyl group, has higher electron mobility than conventional electron transport materials, has excellent hole blocking property, and is stable in a thin film state.

The compound represented by general formula (1) of the invention, which has a thiadiazole ring structure substituted with a substituted pyridyl group, can be used as a constituent material for an electron transport layer of an organic EL device. The use of the material having high electron injection/transport rate compared to the conventional materials improves electron transport efficiency from an electron transport layer to an emitting layer to improve luminous efficiency, and decreases driving voltage, thereby providing an effect of improving durability of the organic EL device.

The compound represented by general formula (1) of the invention, which has a thiadiazole ring structure substituted with a substituted pyridyl group, can also be used as a constituent material for a hole blocking layer of an organic EL device. The use of the material having excellent hole blocking property compared to the conventional materials, and being excellent in electron transport properties and having high stability in a thin film state decreases driving voltage while having high luminous efficiency to improve current resistance, thereby providing an effect of improving maximum light emission luminance of the organic EL device.

The compound represented by general formula (1) of the invention, which has a thiadiazole ring structure substituted with a substituted pyridyl group, can also be used as a constituent material for an emitting layer of an organic EL device. The use of an emitting layer using the material of the invention excellent in electron transport properties compared to the conventional materials and having a wide band gap as a host material, and allowing it to carry a fluorescent substance or a phosphorescence-emitting substance called a dopant, provides an effect of realizing an organic EL device decreased in driving voltage and improved in luminous efficiency.

The organic EL device of the invention uses the compound having a thiadiazole ring structure substituted with a plurality of connected pyridyl groups, which has higher electron mobility than the conventional electron transport materials, has excellent hole blocking property, and is stable in a thin film state. It becomes therefore possible to realize high efficiency and high durability.

Advantages of the Invention

The invention relates to a compound having a thiadiazole ring structure substituted with a substituted pyridyl group, which is useful as a constituent material for an electron transport layer, a hole blocking layer or an emitting layer of an organic EL device, and an organic EL device prepared using the compound. According to the invention, luminous efficiency and durability can be improved, compared to conventional organic EL devices.

Figure 1:
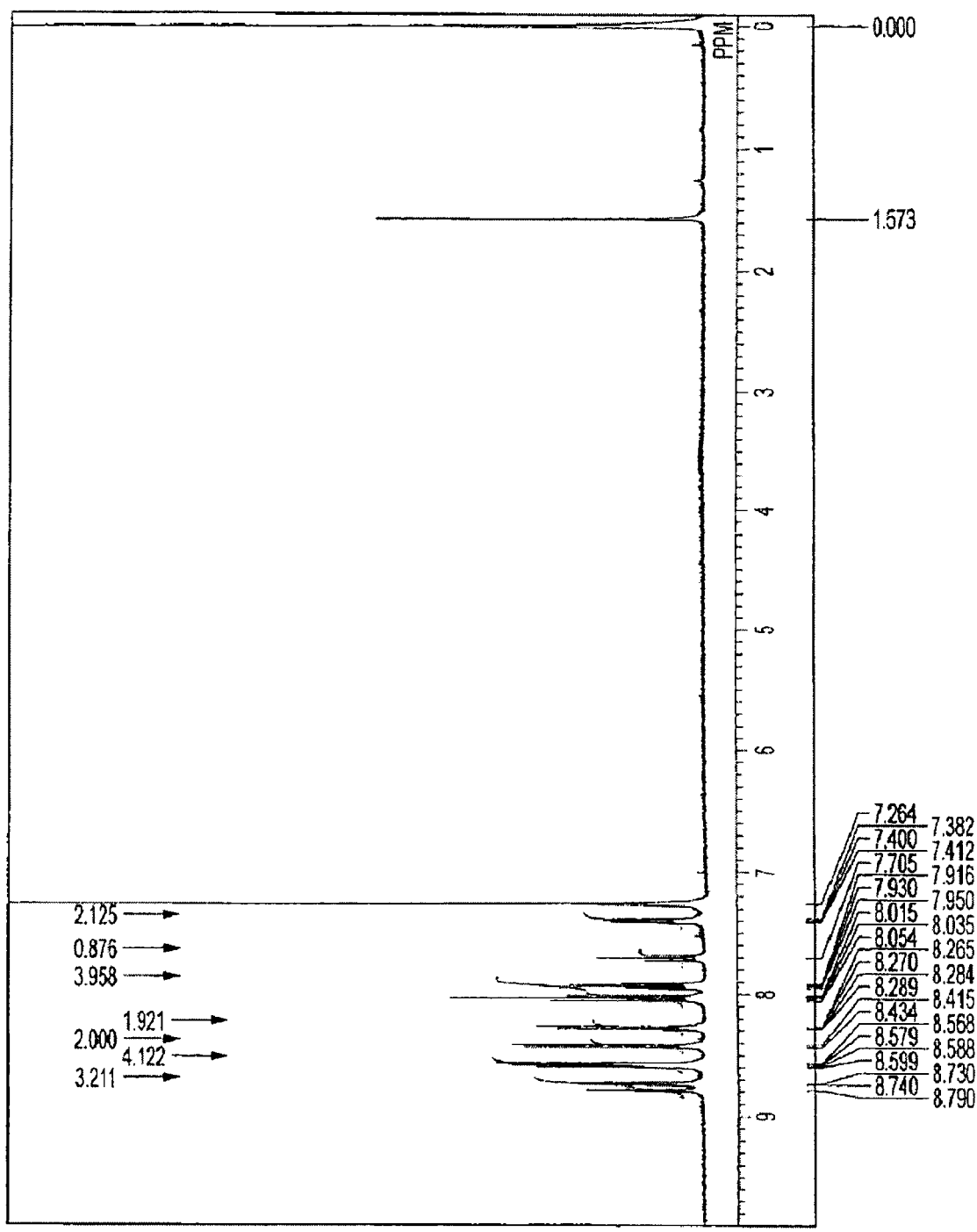
FIG. 1 is a $^1$H-NMR chart of BpyTHDm.

| DESCRIPTION OF REFERENCE NUMERALS AND SIGNS | |
|---|---|
| 1 | Glass Substrate |
| 2 | Transparent Anode |
| 3 | Hole Injection Layer |
| 4 | Hole Transport Layer |
| 5 | Emitting Layer |
| 6 | Hole Blocking Layer |
| 7 | Electron Transport Layer |
| 8 | Cathode |

BEST MODE FOR CARRYING OUT THE INVENTION

The compound of the invention which has a thiadiazole ring structure substituted with a substituted pyridyl group is a novel compound. The compound having a thiadiazole ring structure having connected thereto a substituted pyridyl group can be synthesized, for example, by conducting a cyclization reaction of a corresponding N,N'-dihydrazide with a Lawson reagent (for example, see non-patent document 4) or diphosphorus pentasulfide (for example, see non-patent document 5).

Non-Patent Document 4: Bull. Soc. Chim. France, p. II-62 (1985)

Non-Patent Document 5: J. prakt. Chem. 322, 933 (1980)

Of the compounds represented by general formula (1), which have a thiadiazole ring structure substituted with a substituted pyridyl group, specific examples of preferred compounds are shown below, but the invention is not limited to these compounds.

[Chem. 2]

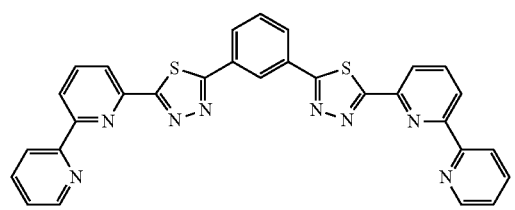

(2)

[Chem. 3]

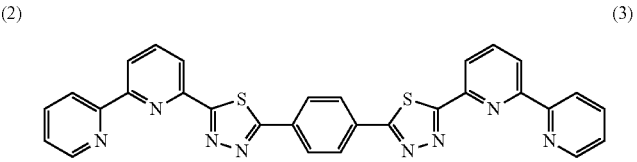

(3)

[Chem. 4]

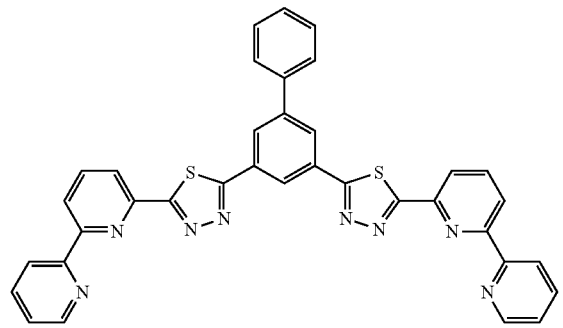

(4)

[Chem. 5]

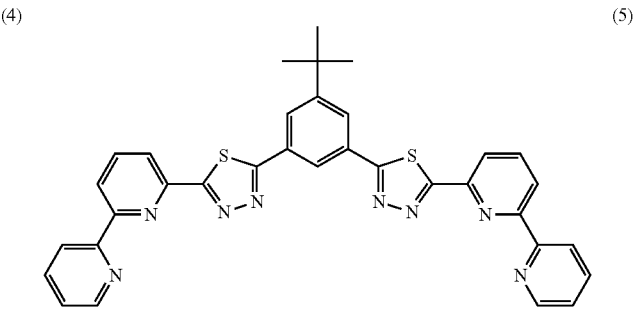

(5)

-continued
[Chem. 6]
(6)
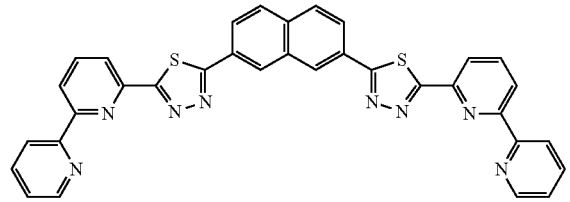
[Chem. 7]
(7)
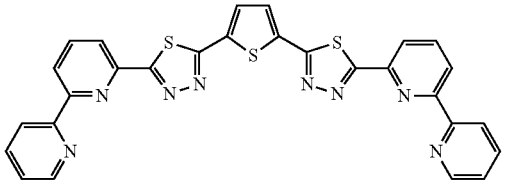
[Chem. 8]
(8)
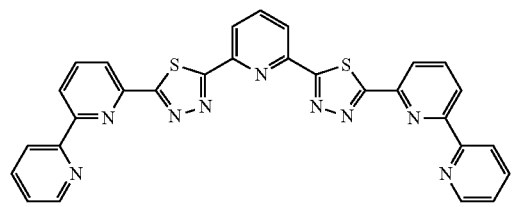
[Chem. 9]
(9)
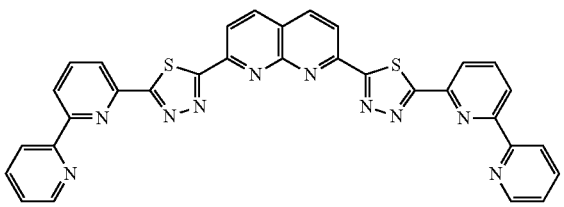
[Chem. 10]
(10)
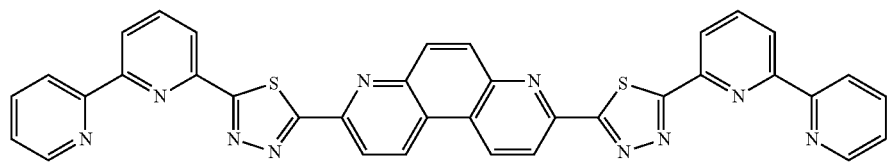
[Chem. 11]
(11)
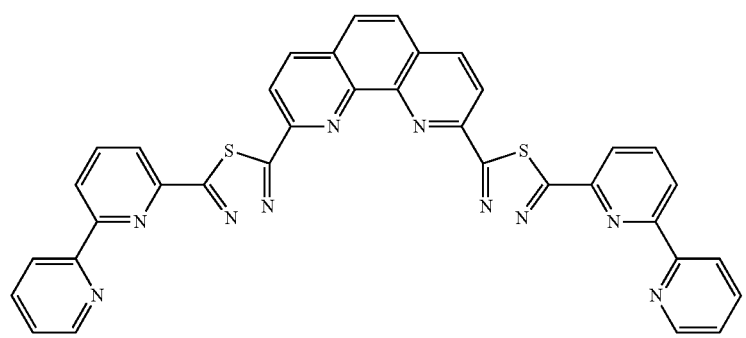
[Chem. 12]
(12)
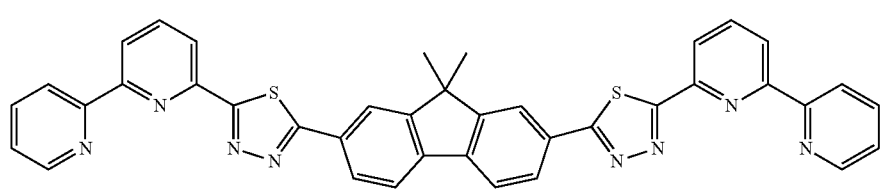

[Chem. 13]
(13)
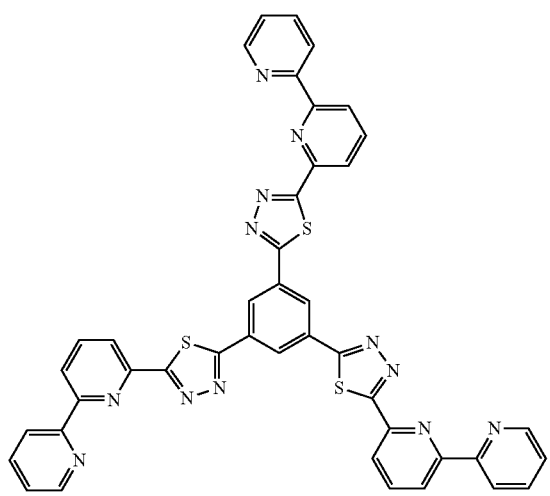
[Chem. 14]
(14)
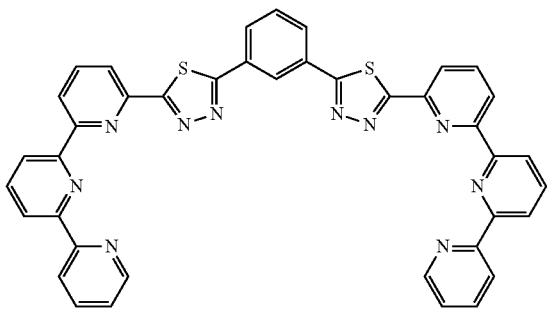
[Chem. 15]
(15)
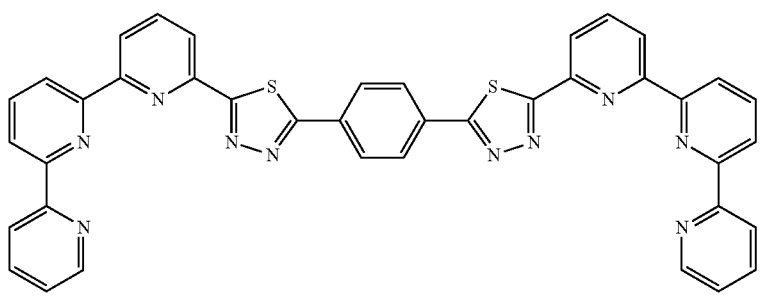
[Chem. 16]
(16)
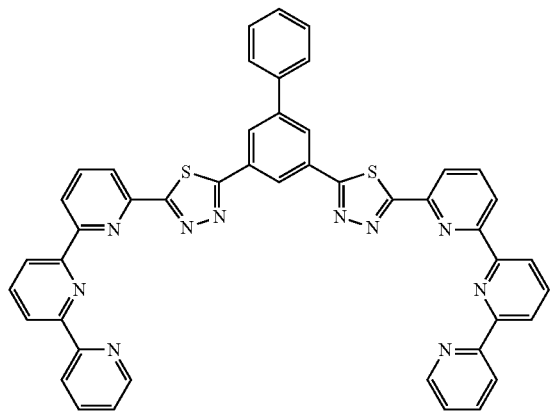
[Chem. 17]
(17)
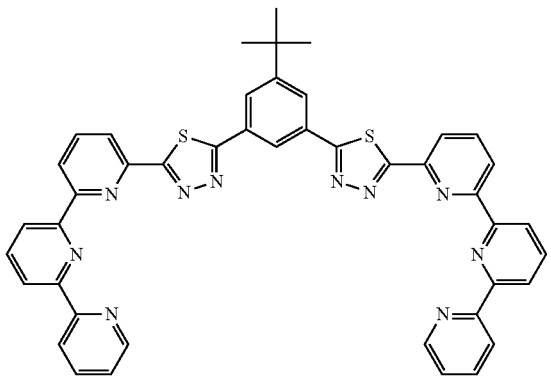

-continued
[Chem. 18]
(18)
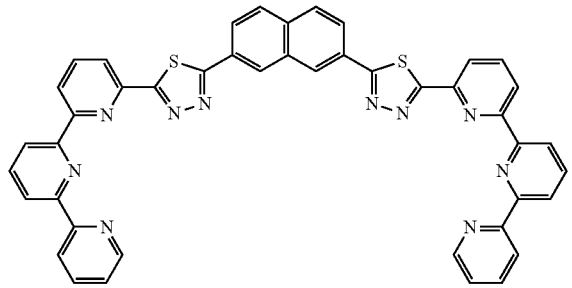
[Chem. 19]
(19)
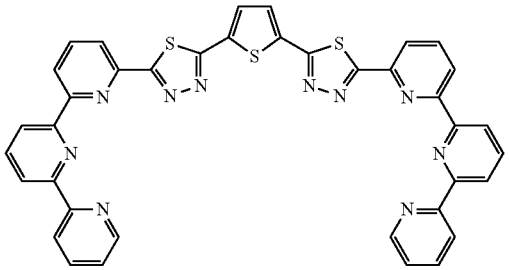
[Chem. 20]
(20)
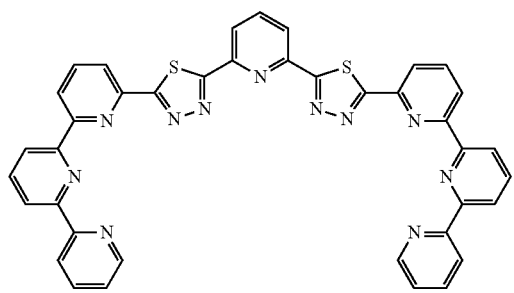
[Chem. 21]
(21)
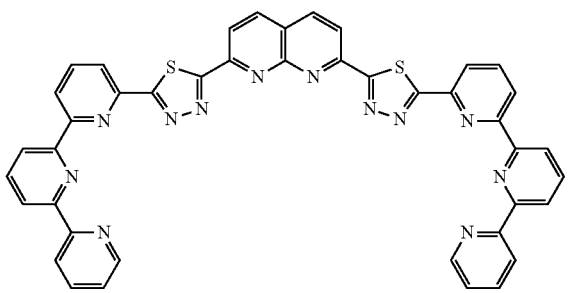
[Chem. 22]
(22)
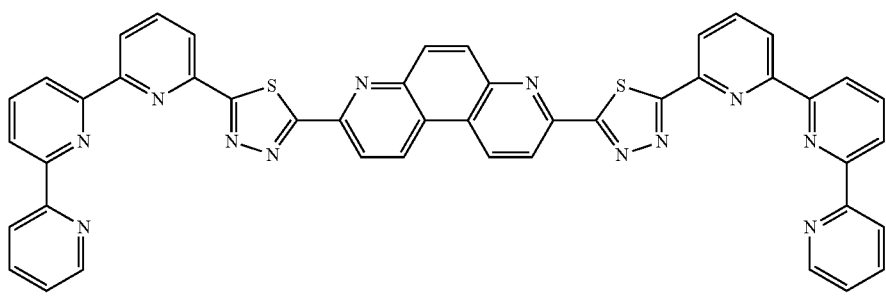
[Chem. 23]
(23)
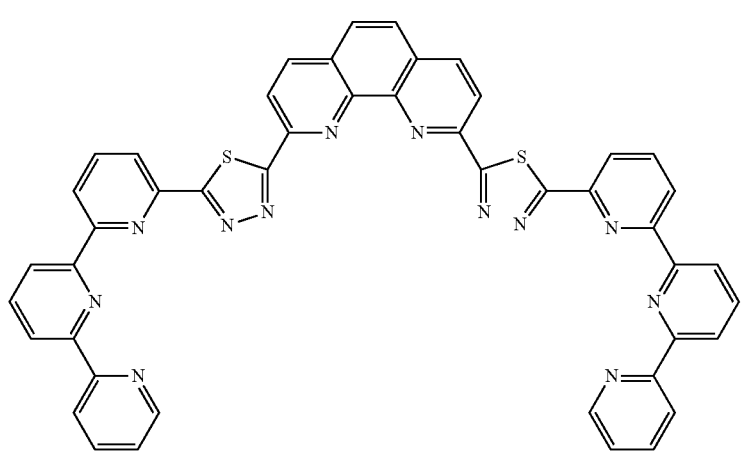

-continued
[Chem. 24]
(24)
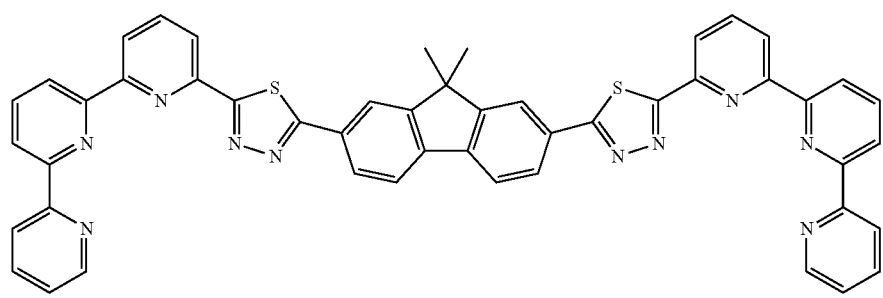
[Chem. 25]
(25)
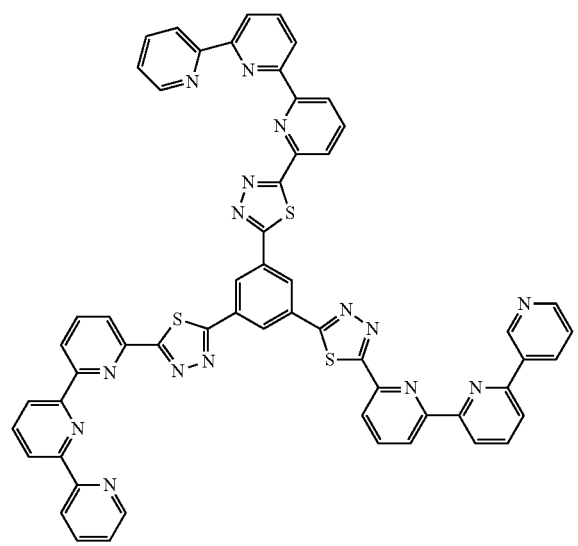
[Chem. 26]
(26)
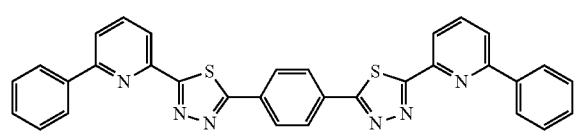
[Chem. 27]
(27)
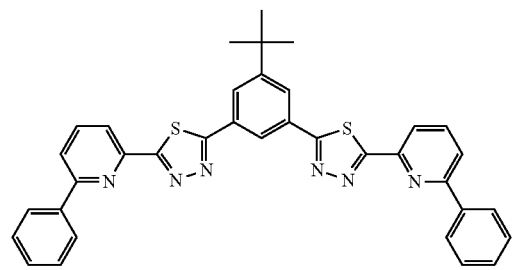
[Chem. 28]
(28)
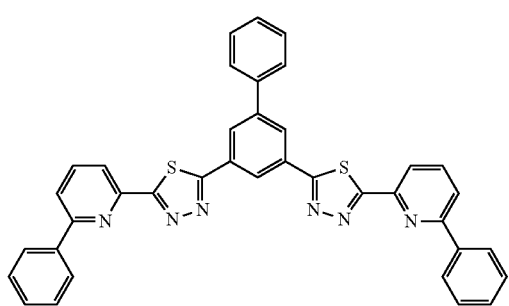
[Chem. 29]
(29)
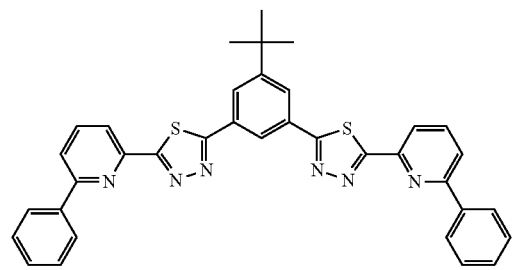
[Chem. 30]
(30)
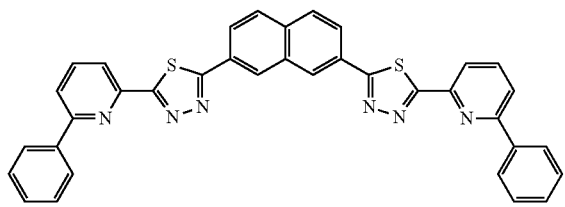

-continued
[Chem. 31]
(31)
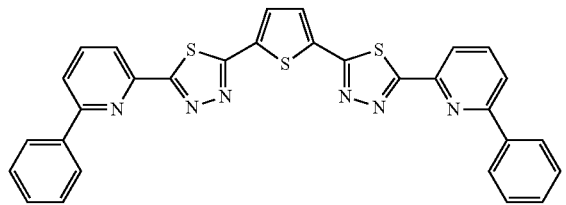
[Chem. 32]
(32)
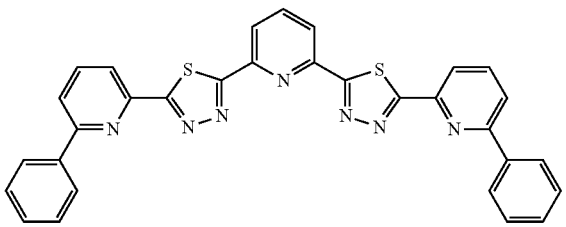
[Chem. 33]
(33)
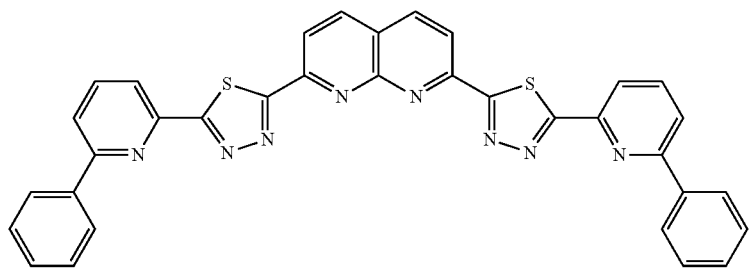
[Chem. 34]
(34)
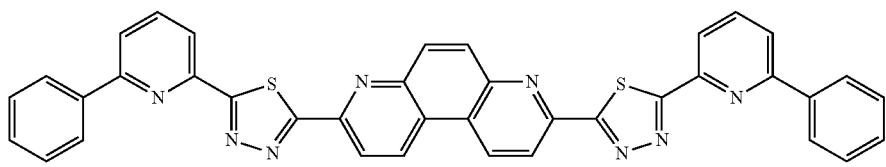
[Chem. 35]
(35)
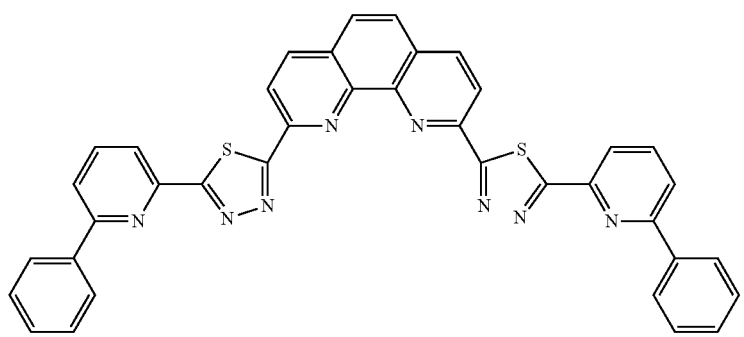
[Chem. 36]
(36)
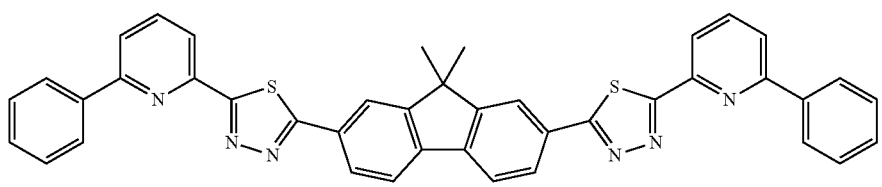

[Chem. 37]
(37)
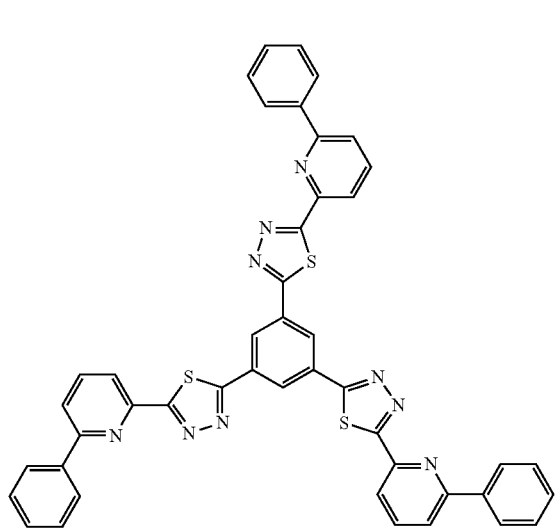
[Chem. 38]
(38)
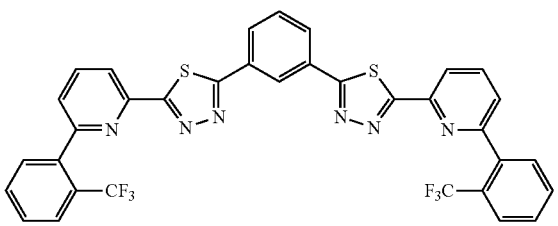
[Chem. 39]
(39)
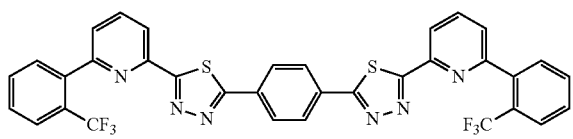
[Chem. 40]
(40)
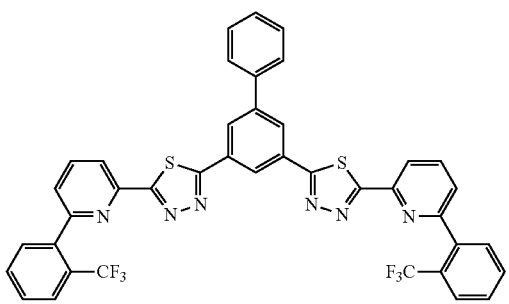
[Chem. 41]
(41)
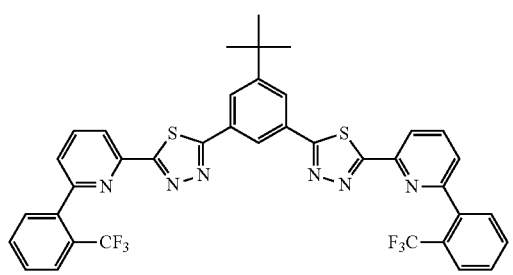
[Chem. 42]
(42)
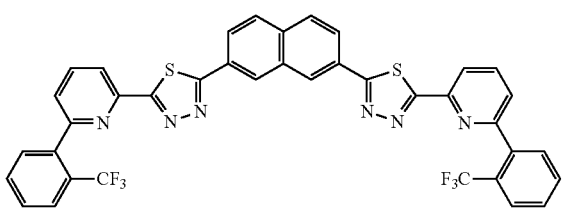
[Chem. 43]
(43)
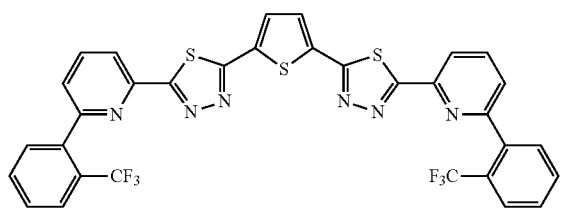
[Chem. 44]
(44)
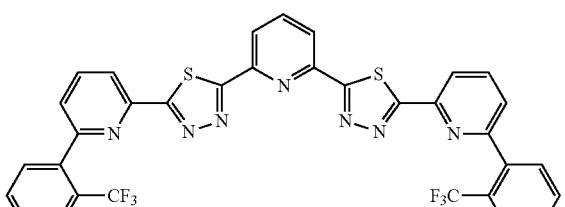

-continued
[Chem. 45]
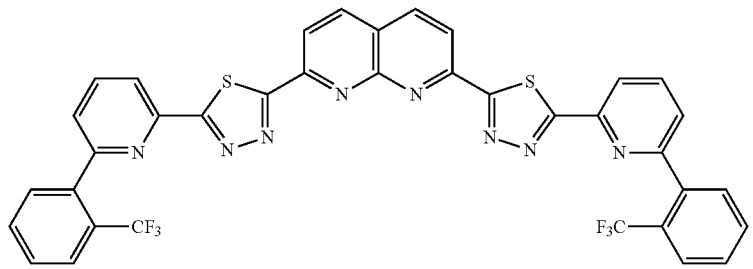
(45)
[Chem. 46]
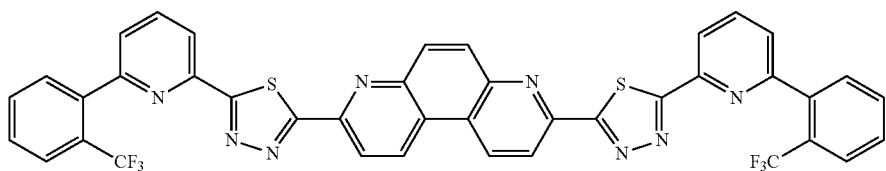
(46)
[Chem. 47]
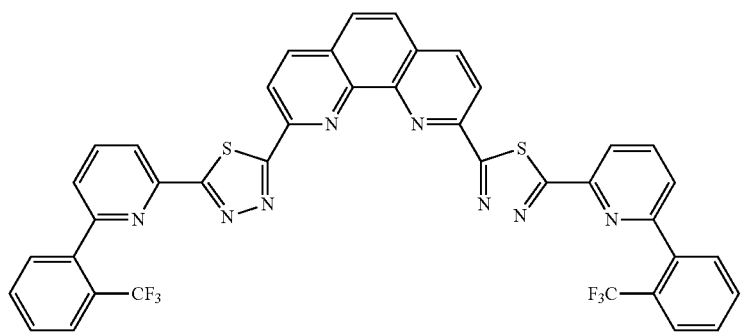
(47)
[Chem. 48]
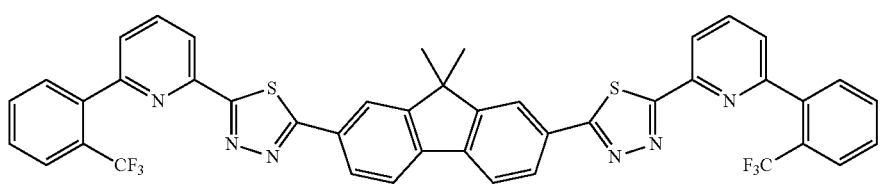
(48)

-continued
[Chem. 49]
(49)
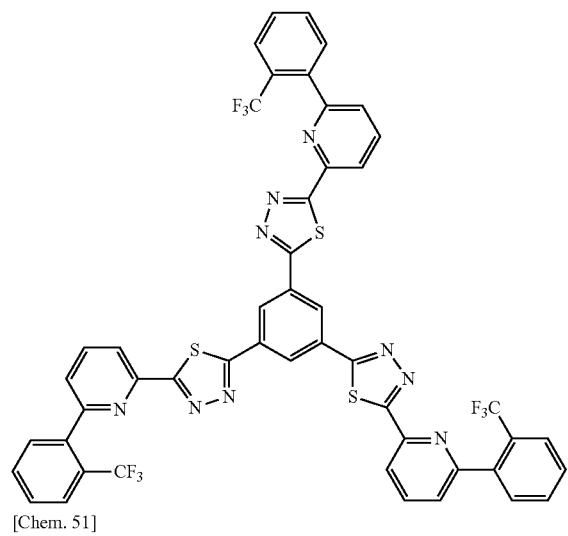
[Chem. 50]
(50)
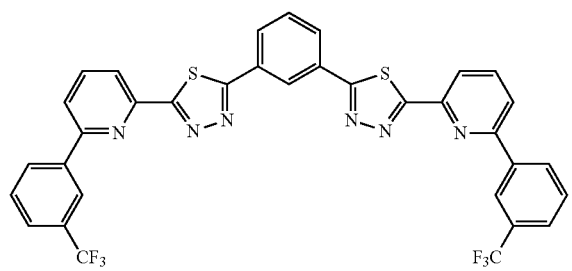
[Chem. 51]
(51)
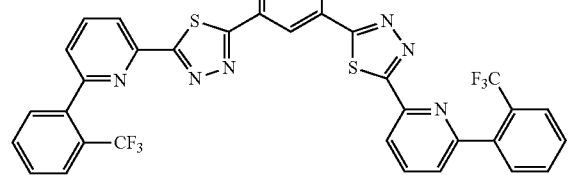
[Chem. 52]
(52)
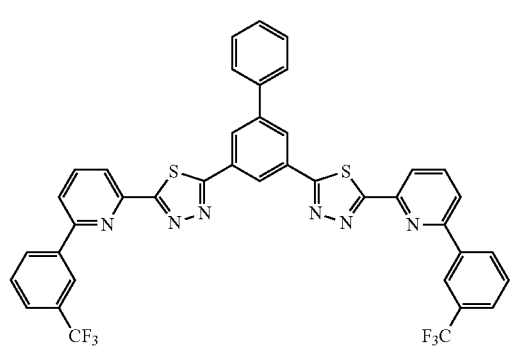
[Chem. 53]
(53)
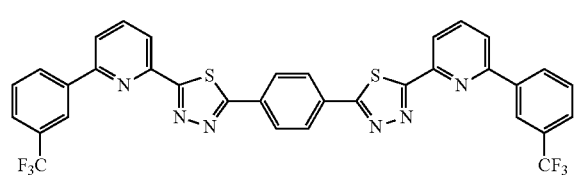
[Chem. 54]
(54)
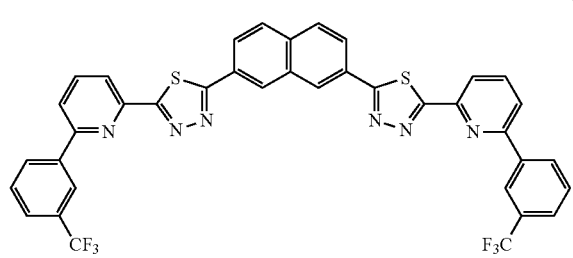
[Chem. 55]
(55)
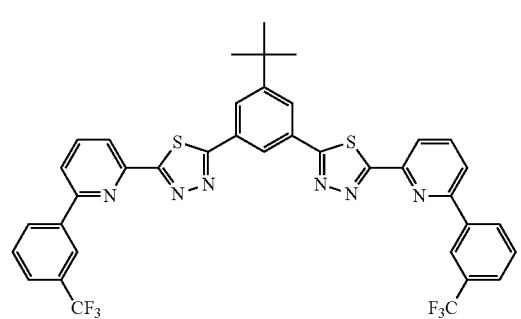
[Chem. 56]
(56)
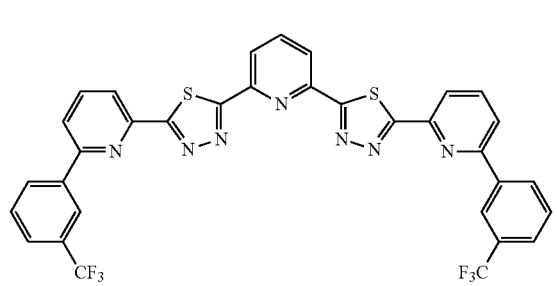
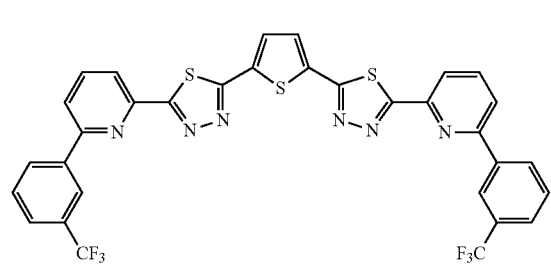

-continued
[Chem. 57]
(57)
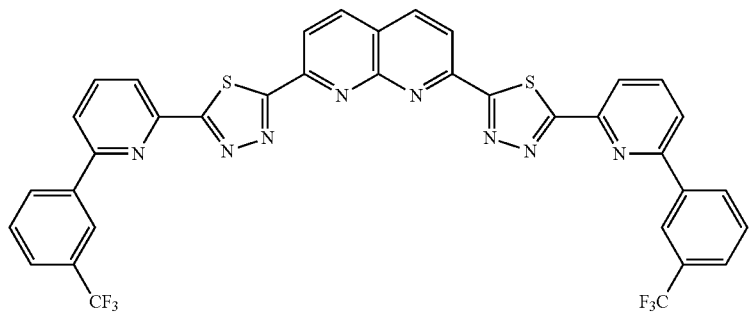
[Chem. 58]
(58)
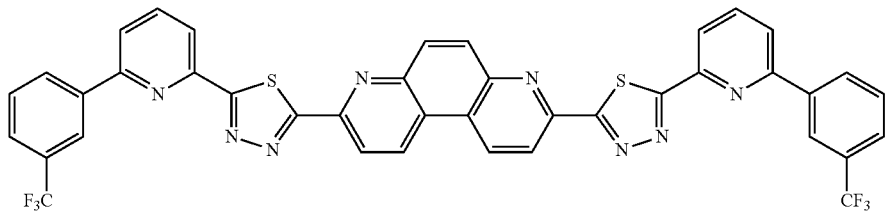
[Chem. 59]
(59)
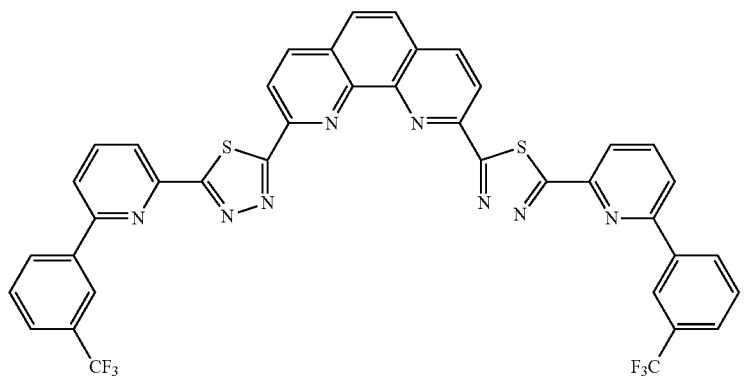
[Chem. 60]
(60)
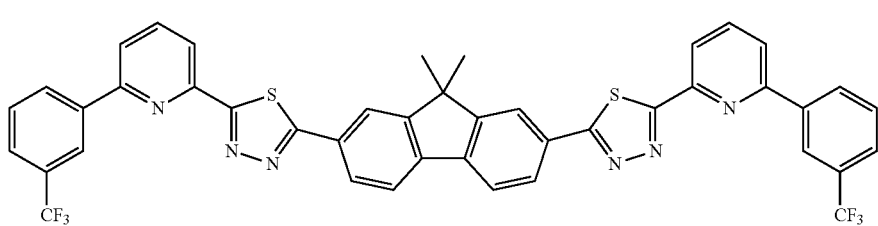

[Chem. 61]
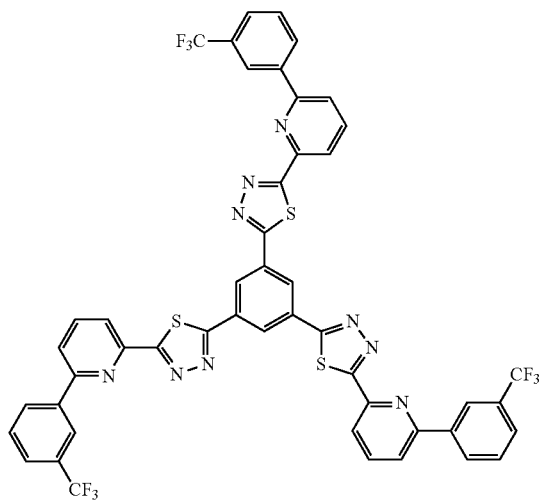
(61)
[Chem. 62]
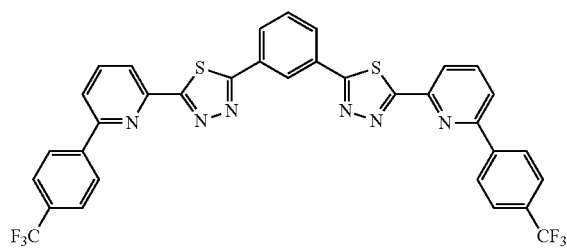
(62)
[Chem. 63]
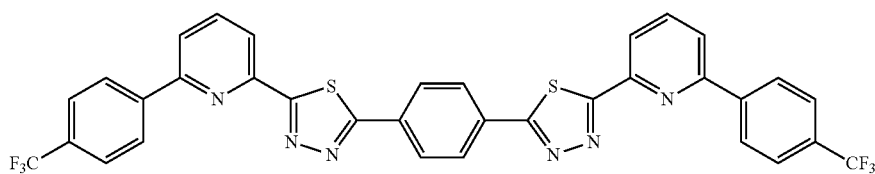
(63)
[Chem. 64]
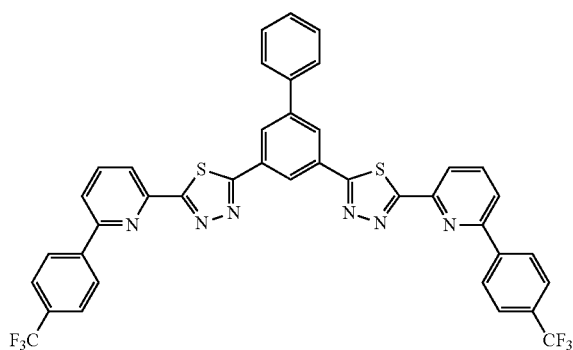
(64)
[Chem. 65]
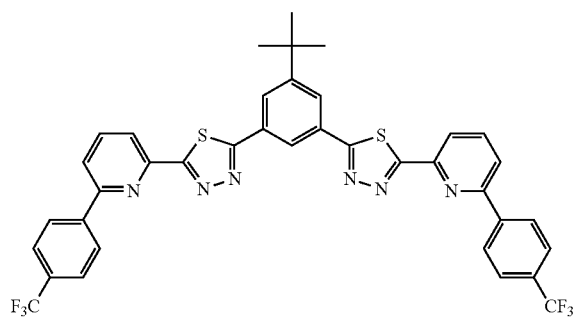
(65)
[Chem. 66]
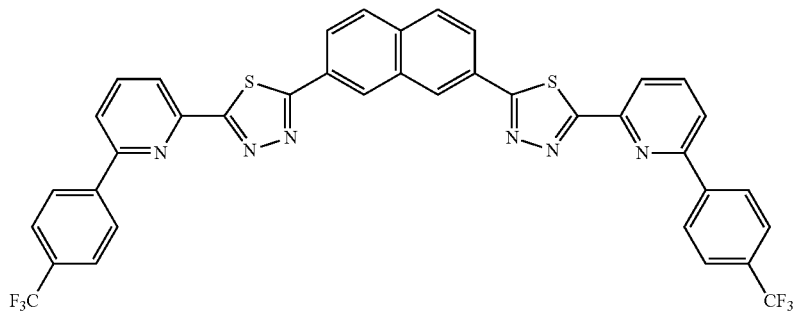
(66)

[Chem. 67]
(67)
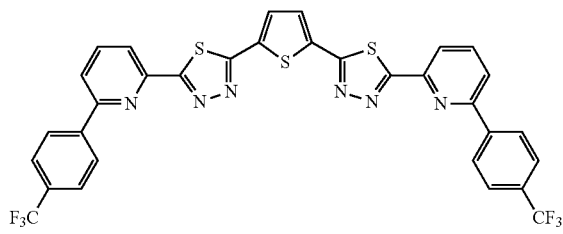
[Chem. 68]
(68)
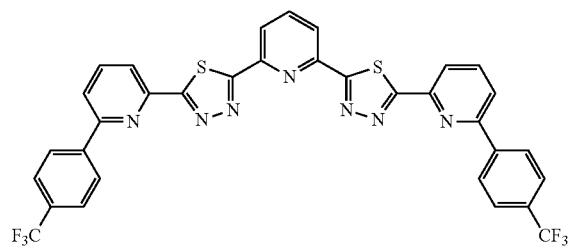
[Chem. 69]
(69)
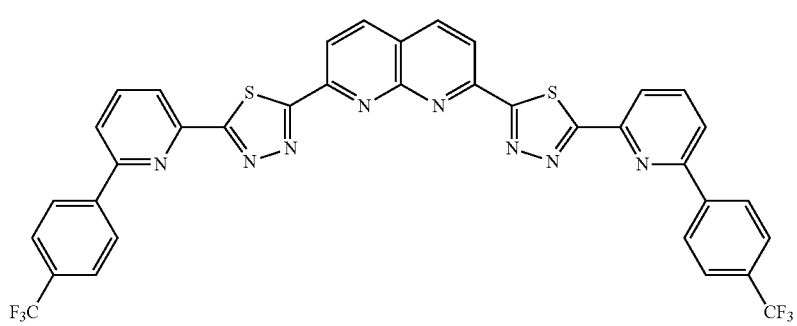
[Chem. 70]
(70)
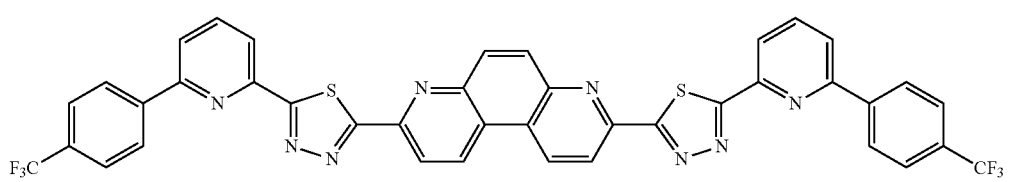
[Chem. 71]
(71)
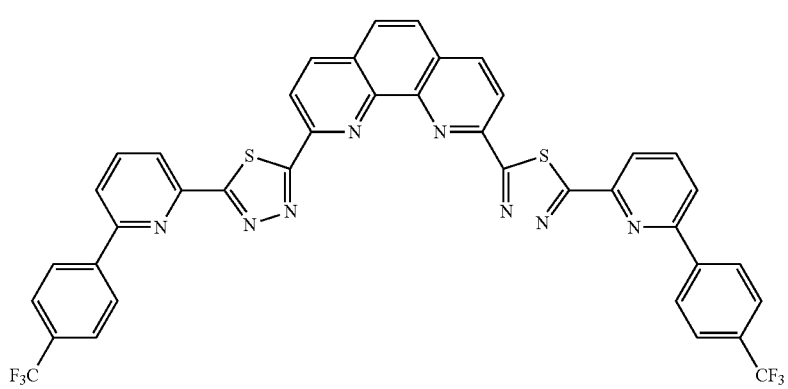
[Chem. 72]
(72)
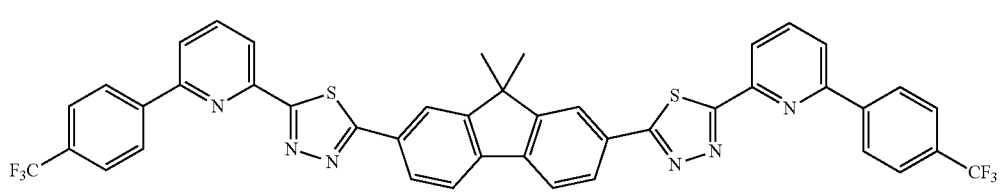

[Chem. 73]
(73)
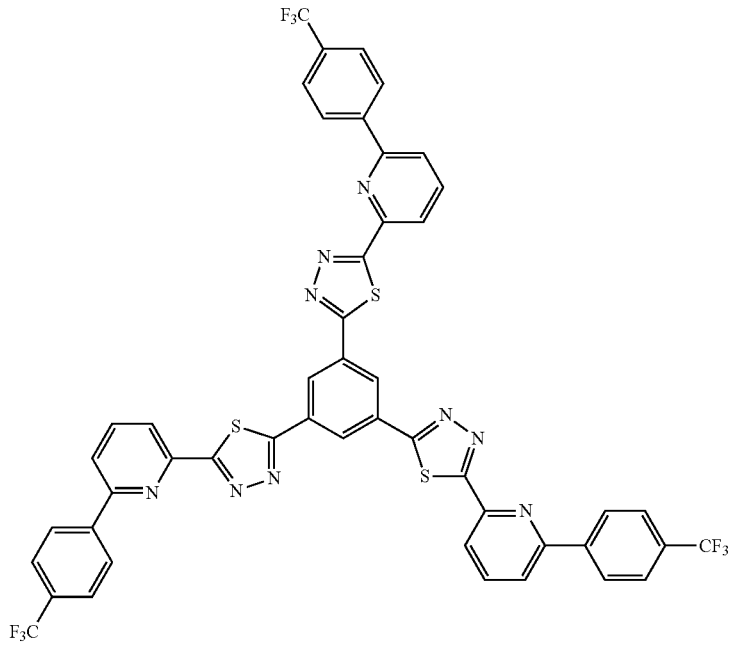
[Chem. 74]
(74)
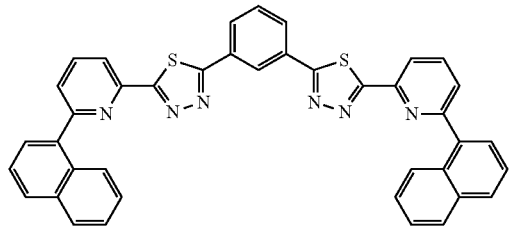
[Chem. 75]
(75)
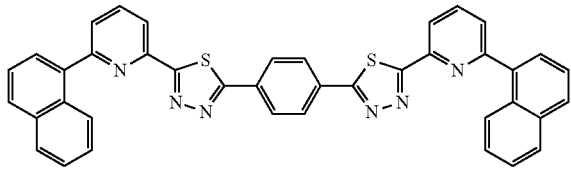
[Chem. 76]
(76)
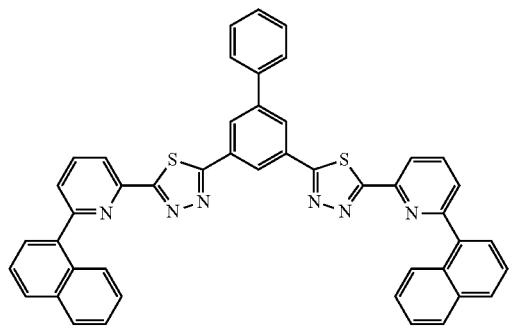
[Chem. 77]
(77)
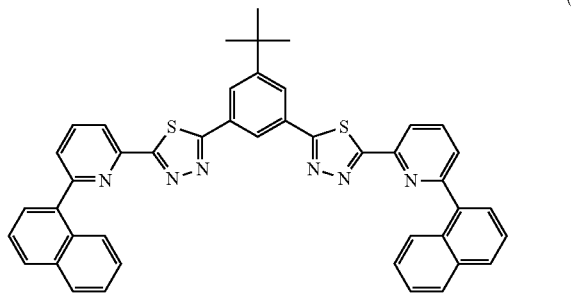
[Chem. 78]
(78)
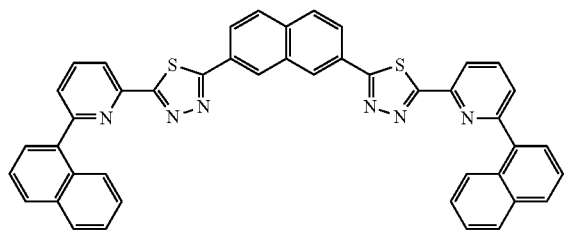
[Chem. 79]
(79)
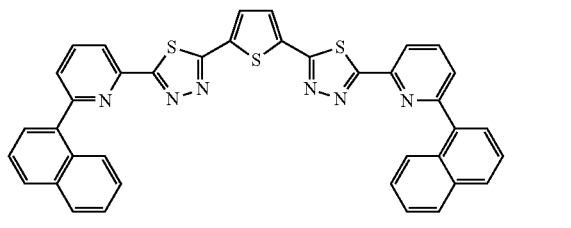

[Chem. 80]
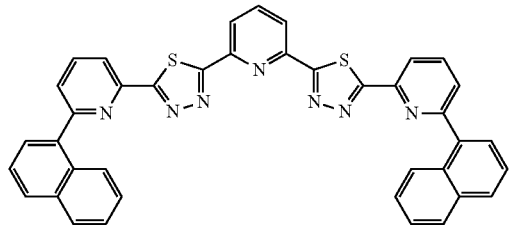
(80)
[Chem. 81]
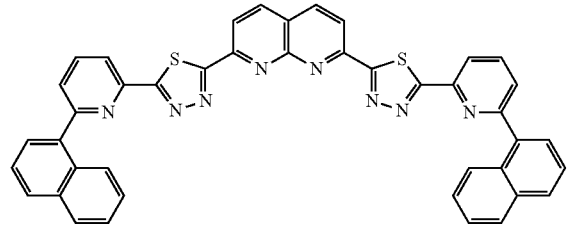
(81)
[Chem. 82]
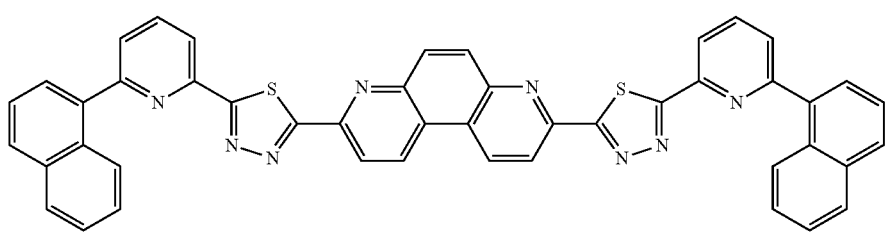
(82)
[Chem. 83]
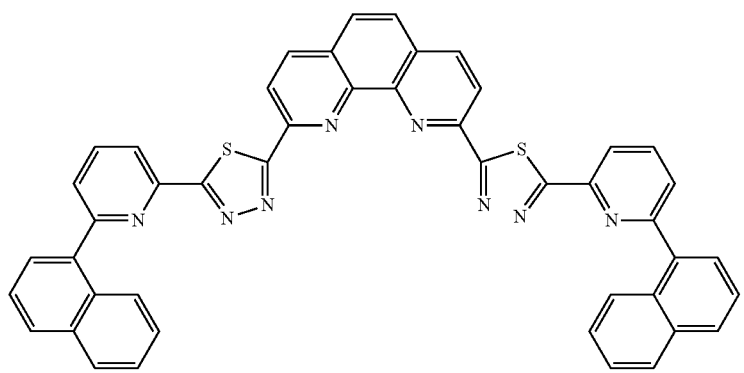
(83)
[Chem. 84]
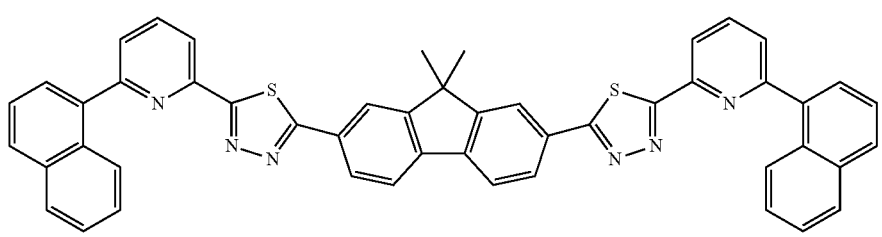
(84)

-continued
[Chem. 85]
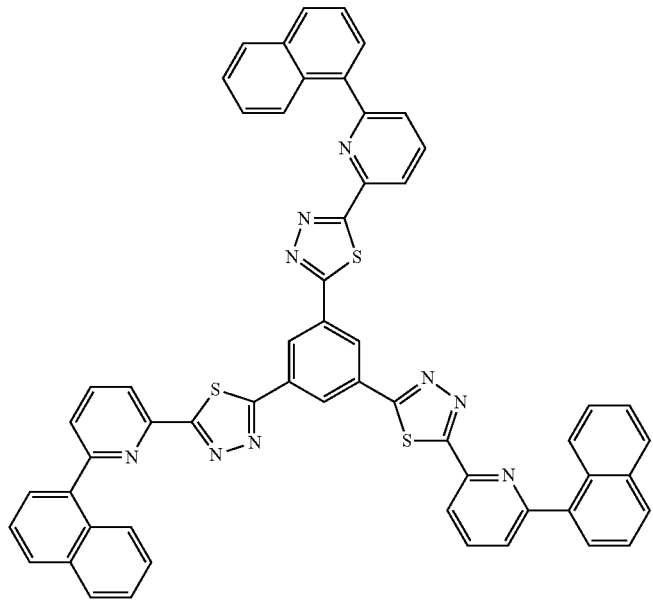
(85)
[Chem. 86]
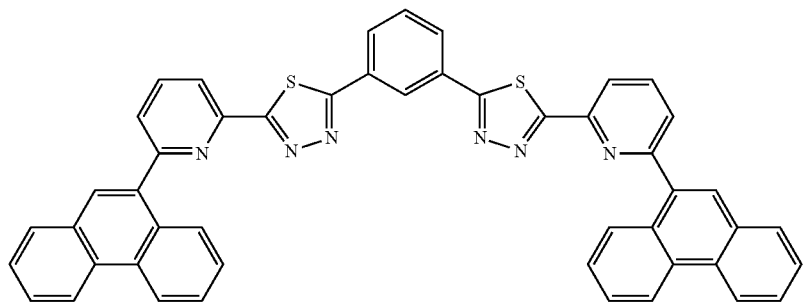
(86)
[Chem. 87]
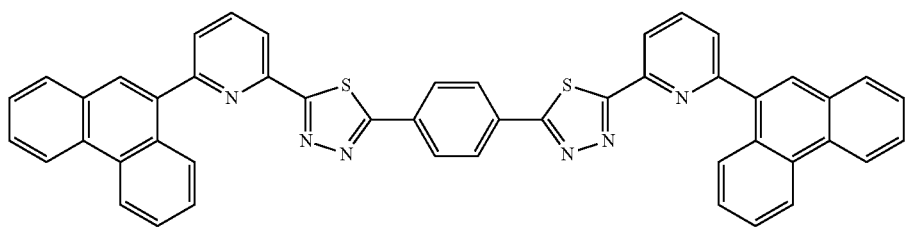
(87)

-continued
[Chem. 88]
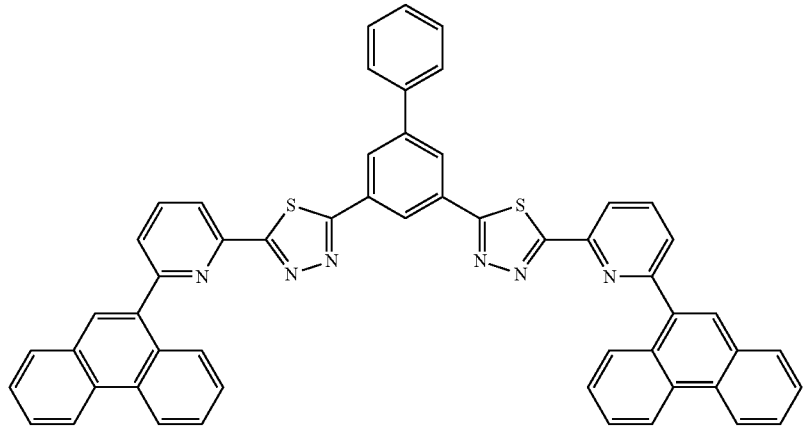
(88)
[Chem. 89]
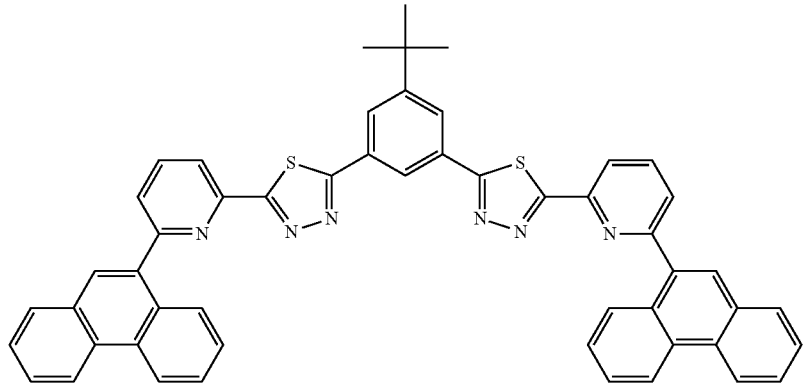
(89)
[Chem. 90]
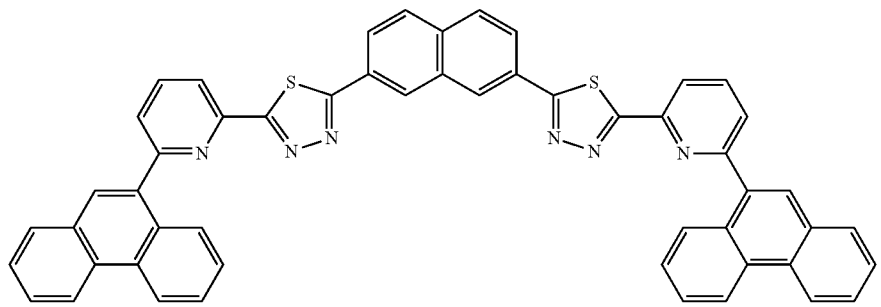
(90)
[Chem. 91]
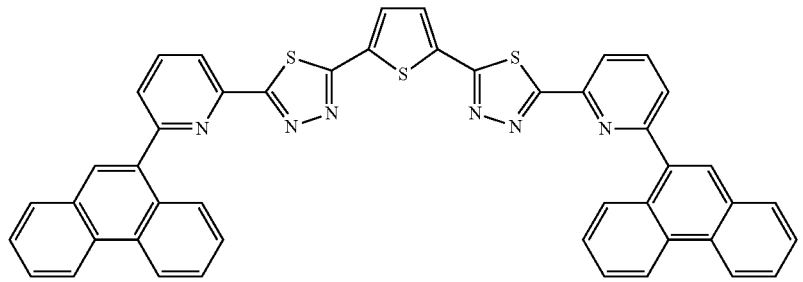
(91)

[Chem. 92]
(92)
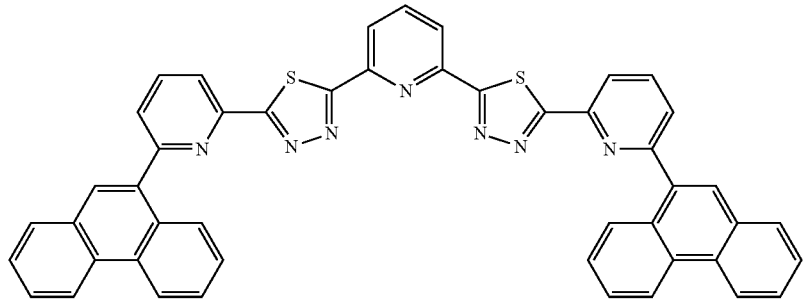
[Chem. 93]
(93)
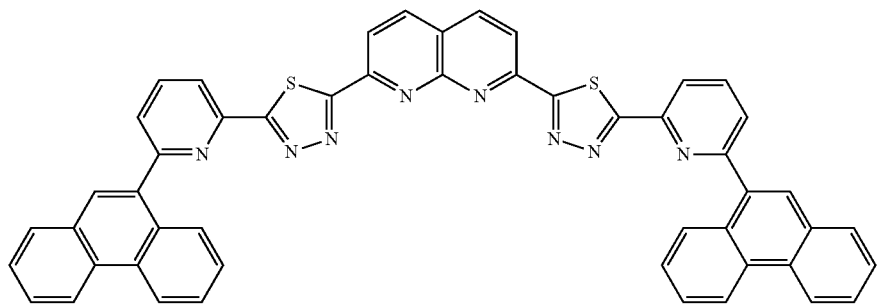
[Chem. 94]
(94)
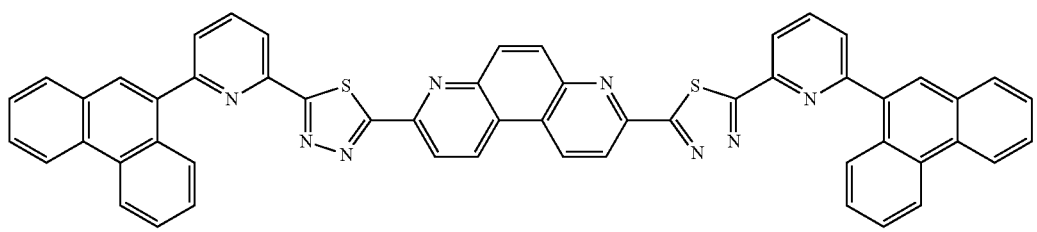
[Chem. 95]
(95)
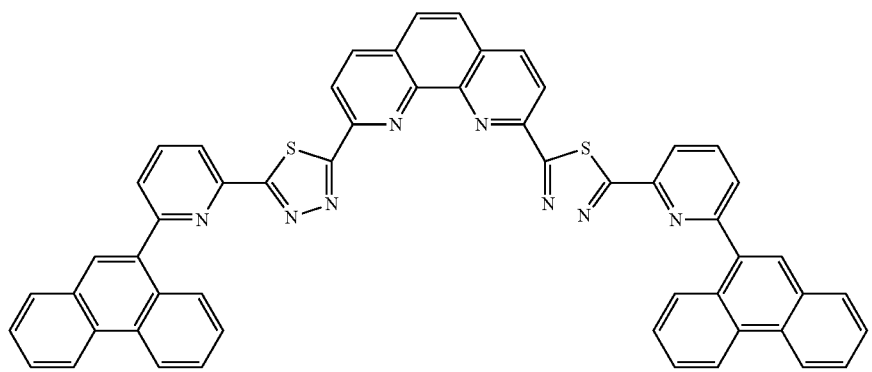
[Chem. 96]
(96)
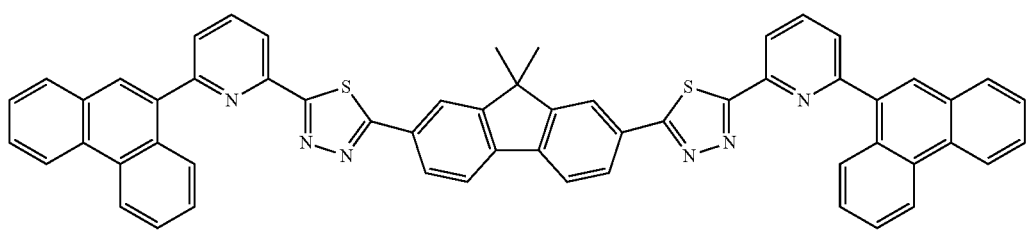

[Chem. 97]
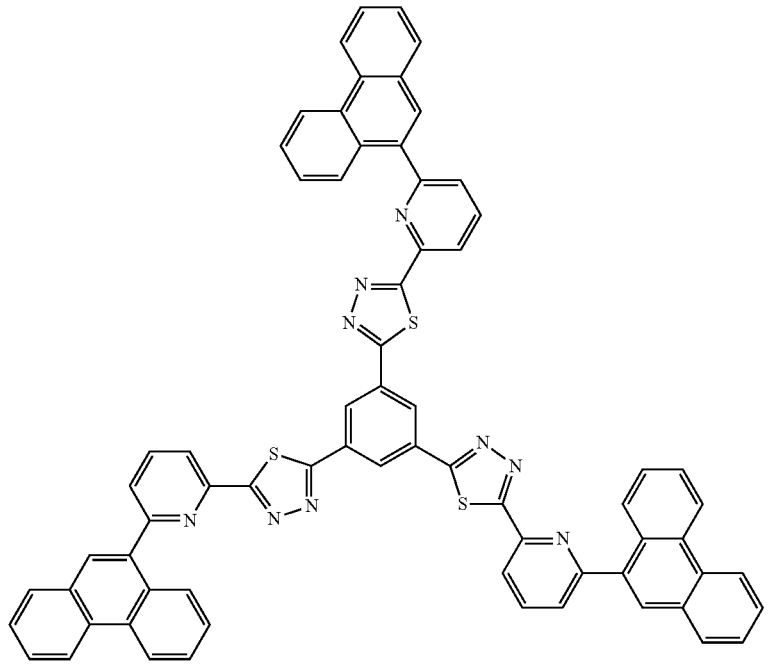
(97)
[Chem. 98]
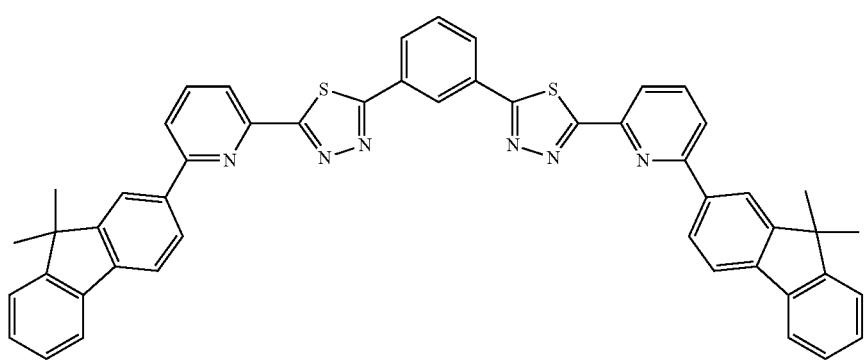
(98)
[Chem. 99]
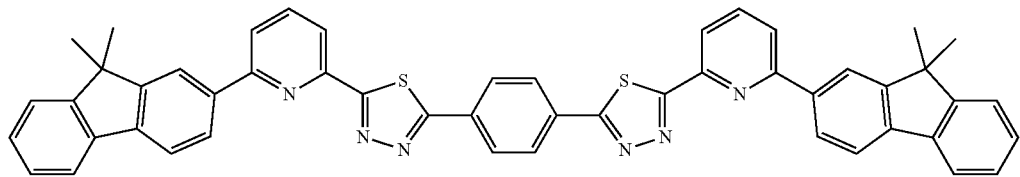
(99)

[Chem. 100]
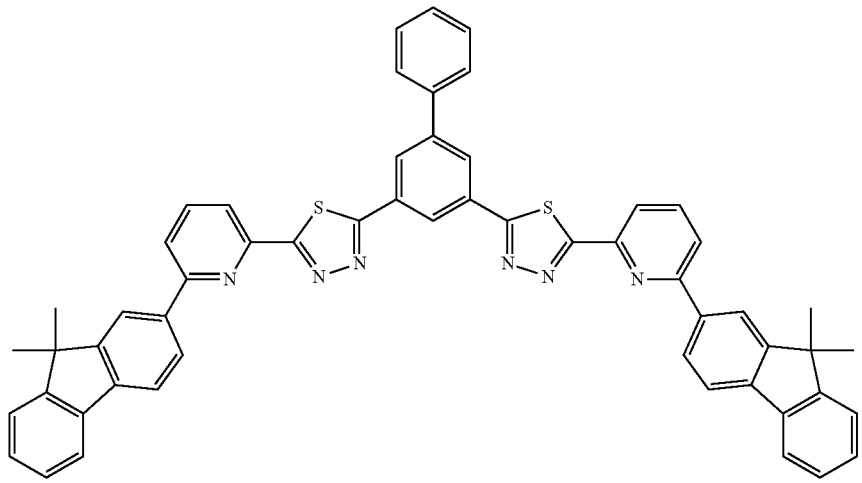
(100)
[Chem. 101]
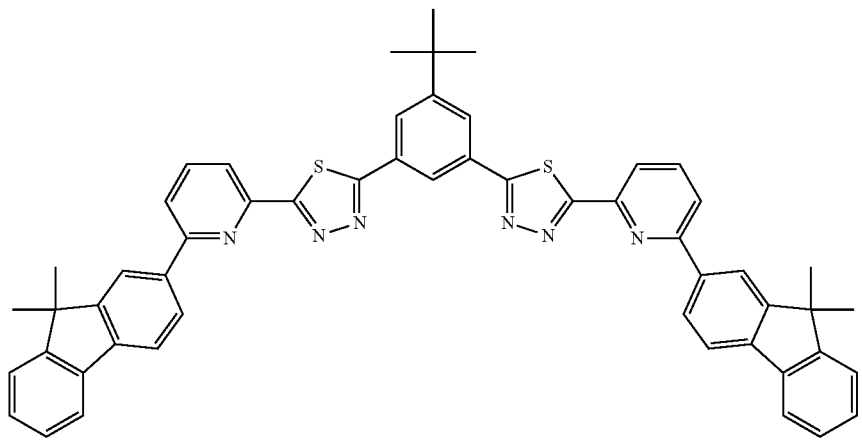
(101)
[Chem. 102]
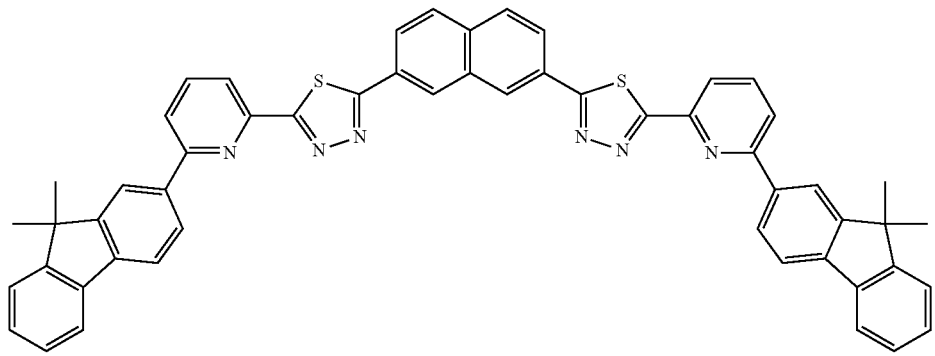
(102)

[Chem. 103]
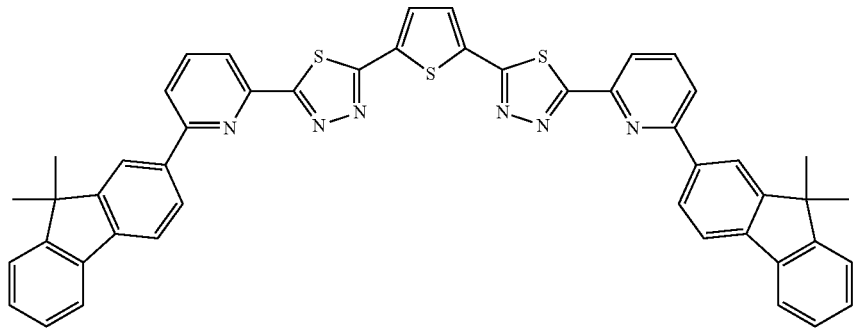
(103)
[Chem. 104]
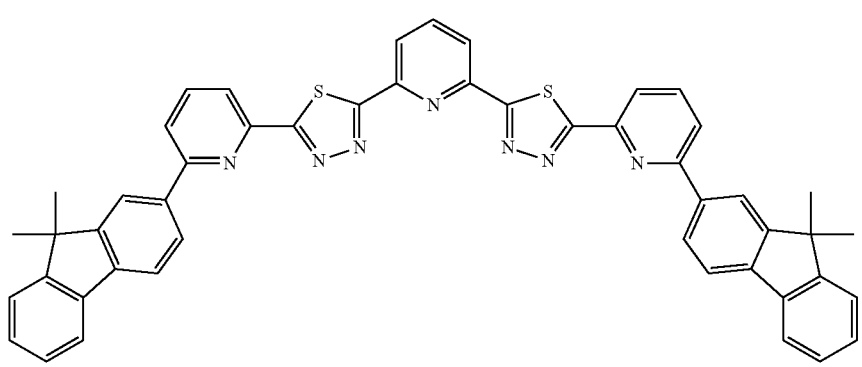
(104)
[Chem. 105]
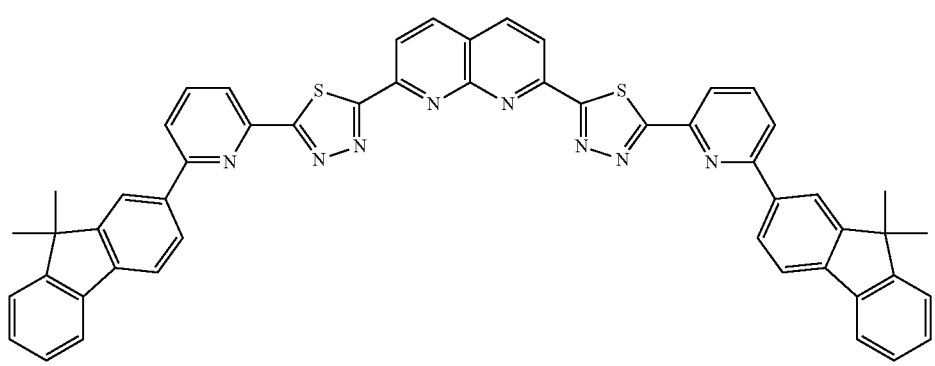
(105)
[Chem. 106]
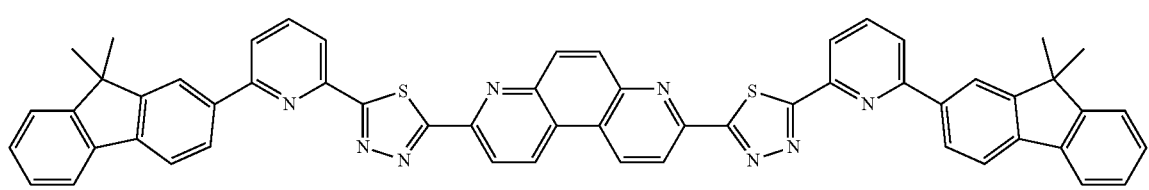
(106)

[Chem. 107]
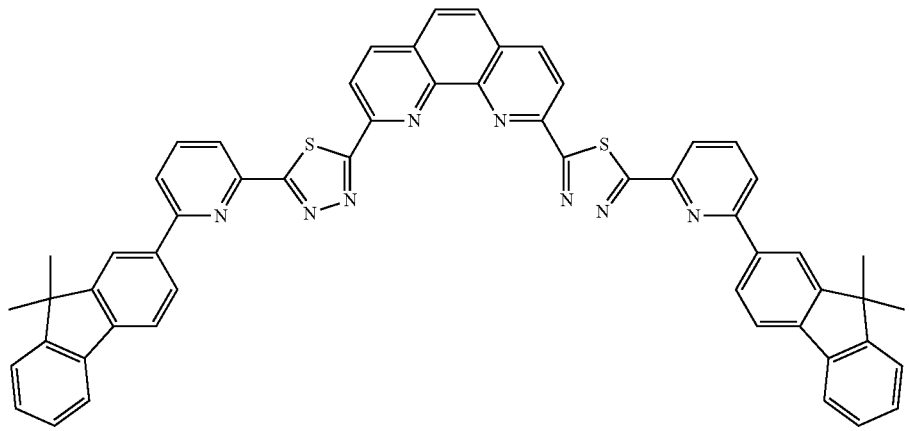
(107)
[Chem. 108]
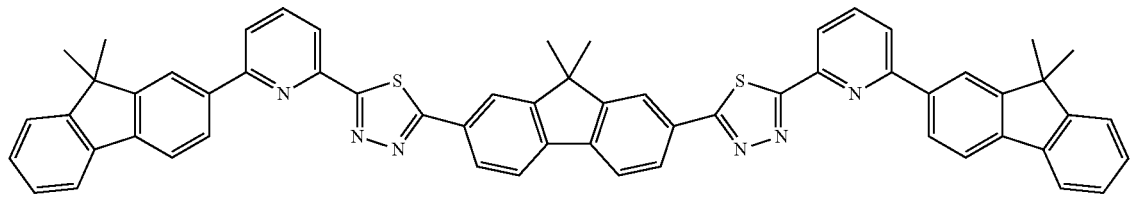
(108)
[Chem. 109]
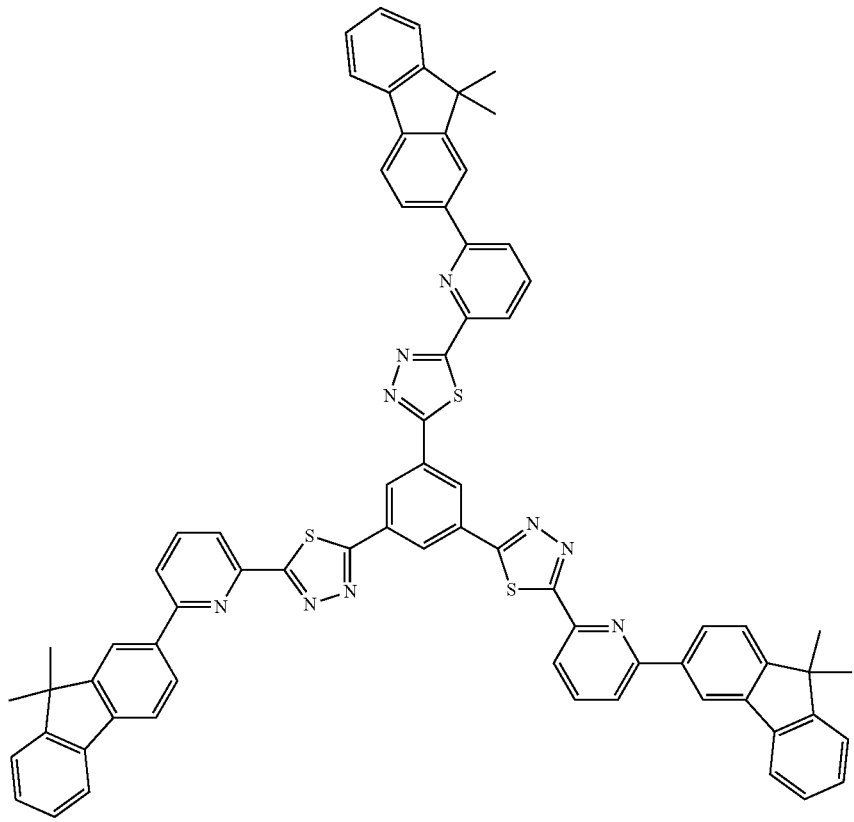
(109)

Purification of these compounds was performed by column chromatograph purification, adsorption purification, recrystallization using a solvent, a crystallization method or the like. Identification of the compounds was performed by NMR analysis. For physical property values, DSC measurement (Tg) and measurement of the melting point were performed. The melting point serves as an index of vapor deposition properties, and the glass transition point (Tg) serves as an index of stability in a thin film state.

The melting point and the glass transition point were measured using a powder with a highly sensitive differential scanning calorimeter DSC3100S, manufactured by Bruker AXS K.K.

Further, the work function was measured by preparing a 100-nm thin film on an ITO substrate and using an atmospheric photoelectron spectrometer, AC2, manufactured by Riken Keiki Co., Ltd. The work function serves as an index of hole blocking property.

Examples of the structure of the organic EL device of the invention include a structure comprising an anode, a hole injection layer, a hole transport layer, an emitting layer, a hole blocking layer, an electron transport layer and a cathode in this order on a substrate, and a structure further having an electron injection layer between the electron transport layer and the cathode. In these multilayer structures, it is possible to omit some organic layers. For example, the device may have a structure comprising an anode, a hole transport layer, an emitting layer, an electron transport layer and a cathode provided in this order on a substrate.

As the anode of the organic EL device, an electrode material having a large work function, such as ITO or gold may be used. As the hole injection layer, a material such as a starburst type triphenylamine derivative or a coating type material, as well as copper phthalocyanine (hereinafter referred to as CuPc for brevity) may be used.

In the hole transport layer, benzidine derivatives such as N,N'-diphenyl-N,N'-di(m-tolyl)benzidine (hereinafter referred to as TPD for brevity) or N,N'-diphenyl-N,N'-di(α-naphthyl)benzidine (hereinafter referred to as NPD for brevity), various triphenylamine tetramers or the like may be used. Further, as the hole injection/transport layer, coating type polymer materials such as PEDOT/PSS may be used.

As the emitting layer, the hole blocking layer and the electron transport layer of the organic EL device of the invention, an aluminum complex, a thiazole derivative, an oxazole derivative, a carbazole derivative, a polydialkylfluorene derivative or the like may be used as well as the compound having a thiadiazole ring structure substituted with a substituted pyridyl group.

A high-performance organic EL device can be prepared by using a conventional light-emitting material such as an aluminum complex or a styryl derivative for the emitting layer, and using as the hole blocking layer or the electron transport layer the compound having a thiadiazole ring structure substituted with a substituted pyridyl group. Further, a high-performance organic EL device can also be prepared by adding as a host material of the emitting layer a dopant, for example, a fluorescent substance such as quinacridone, cumarin or rubrene, or a phosphorescence-emitting substance such as an iridium complex of phenylpyridine.

Furthermore, the compound having a thiadiazole ring structure substituted with a substituted pyridyl group may be multilayered or co-deposited with a conventional electron-transporting material to be used as the electron transport layer.

The organic EL device of the invention may have an electron injection layer. As the electron injection layer, lithium fluoride or the like can be used. For the cathode, an electrode material having a low work function such as aluminum or an alloy having a lower work function such as aluminum-magnesium is used as the electrode material.

Illustrative embodiments of the invention will be described in detail with reference to the following examples, but the invention should not be construed as being limited thereto so long as not exceeding the gist thereof.

EXAMPLE 1

Synthesis of 1,3-Bis[2-(2,2'-bipyridine-6-yl)-1,3,4-thia-diazole-5-yl]benzene (Hereinafter Referred to as BpyTHDm for Brevity) (2)

N',N'-Bis(2,2'-bipyridine-6-carbonyl)isophthalodi-hydrazide (1.0 g), 1.45 g of a Lawson reagent and 10 ml of dehydrated xylene were added and refluxed under heating for 4 hours. After standing to cool, crystals were separated by filtration to obtain a crude product. The obtained crude product was dissolved in chloroform, and purified by a column chromatograph (carrier: silica gel, eluent: chloroform) to obtain 0.45 g (yield: 46%) of white crystals of BpyTHDm (2). Identification of the product was performed by NMR analysis (see FIG. 1). The results of the NMR analysis (CDCL3) were as follows: 8.79 ppm (1H), 8.74 ppm (2H), 8.60-8.57 ppm (4H), 8.43 ppm (2H), 8.29 ppm (2H), 8.03 ppm (2H), 7.93 ppm (2H), 7.71 ppm (1H), 7.40 ppm (2H).

EXAMPLE 2

A heat resistance test was performed at 300° C. for 1 week. The heat resistance test was performed as follows. A sample (10 mg) was placed in a glass test tube, and the tube was evacuated by a diaphragm pump, followed by sealing the tube. The sealed tube containing the sample was placed in a thermostat set at a predetermined temperature, and allowed to stand. After an elapse of a predetermined period of time, the vacuum sealed tube was broken, and the HPLC purity of the sample was measured. The measurement of the HPLC purity was made under the following measurement conditions: column: Inertsil ODS-SP manufactured by GL Sciences Inc. (internal diameter: 4.6 mm, length: 250 mm), mobile phase: acetonitrile/0.05% (v/v) trifluoroacetic acid aqueous solution=90/10 (v/v), flow rate: 1.0 ml/min, column temperature: 40° C., measurement wavelength: 254 mm. The HPLC purity (peak area percentage, %) was as follows:

|  | Before Test | After 1 Week at 300° C. |
| --- | --- | --- |
| BpyTHDm (2) | 99.2% | 98.9% |
| Comparative Compound 1 | 99.9% | 94.2% |

It is apparent that BpyTHDm (2) is excellent in heat resistance compared to the following comparative compound 1.

[Chem. 110]

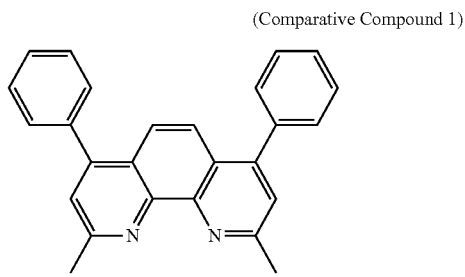

(Comparative Compound 1)

EXAMPLE 3

Synthesis of 2,6-Bis[2-(2,2'-bipyridine-6-yl)-1,3,4-thia-diazole-5-yl]pyridine (Hereinafter Referred to as BpyTHDpy for Brevity) (8)

Figure 2:
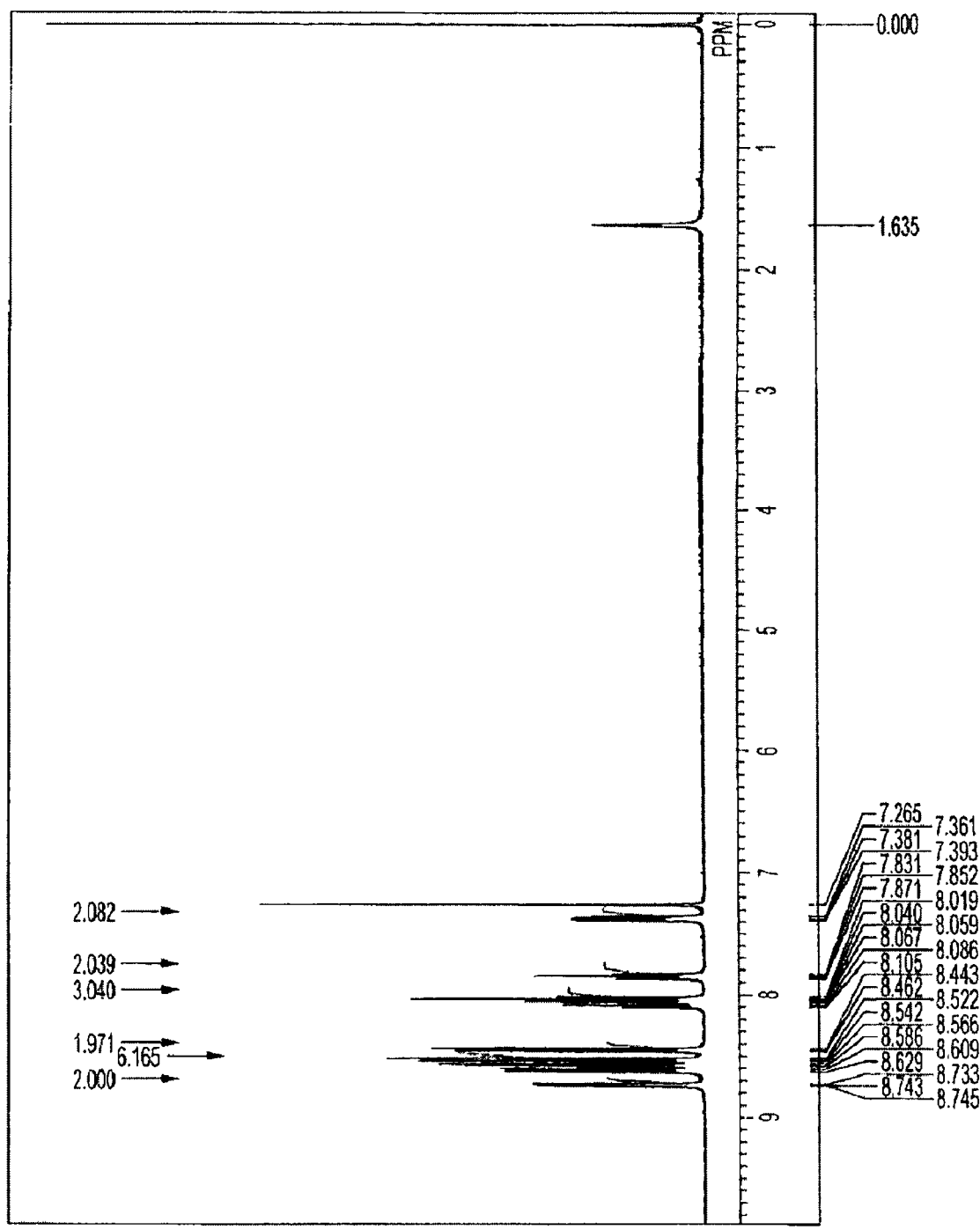
FIG. 2 is a $^1$H-NMR chart of BpyTHDpy.

N',N'-Bis(2,2'-bipyridine-6-carbonyl)-2,6-pyridinedihydrazide (1.0 g), 1.45 g of a Lawson reagent and 20 ml of dehydrated xylene were added and refluxed under heating for 8 hours. After standing to cool, crystals were separated by filtration to obtain a crude product. The obtained crude product was dissolved in chloroform, and purified by a column chromatograph (carrier: silica gel, eluent: chloroform) to obtain 0.40 g (yield: 40%) of white crystals of BpyTHDpy (8). Identification of the product was performed by NMR analysis (see FIG. 2). The results of the NMR analysis (CDCL3) were as follows: 8.75 ppm (2H), 8.64-8.53 ppm (6H), 8.47-8.45 ppm (2H), 8.12-8.00 ppm (3H), 7.88-7.84 ppm (2H), 7.41-7.37 ppm (2H).

EXAMPLE 4

For the compounds of the invention, the melting point and the glass transition point were determined with a highly sensitive differential scanning calorimeter (manufactured by Bruker AXS K.K., DSC3100S).

|  | Melting Point | Glass Transition Point |
| --- | --- | --- |
| BpyTHDm (2) | 310.8° C. | 116.6° C. |
| BpyTHDpy (8) | 347.0° C. | Not observed |

The compounds of the invention have a high glass transition point or no glass transition point, and are stable in a thin film state.

EXAMPLE 5

Using each of the compounds of the invention, a vapor-deposited film having a film thickness of 100 nm was prepared on an ITO substrate, and the work function was measured with an atmospheric photoelectron spectrometer (AC2, manufactured by Riken Keiki Co., Ltd.). The resulting values of the compounds (BpyTHDm and BpyTHDpy) of the invention were both exceeding 6.2 eV which is a measurement limit of the measuring device.

As shown above, the compound of the invention has an apparently deeper work function than the hole transport material, and has great hole blocking property.

EXAMPLE 6

Figure 3:
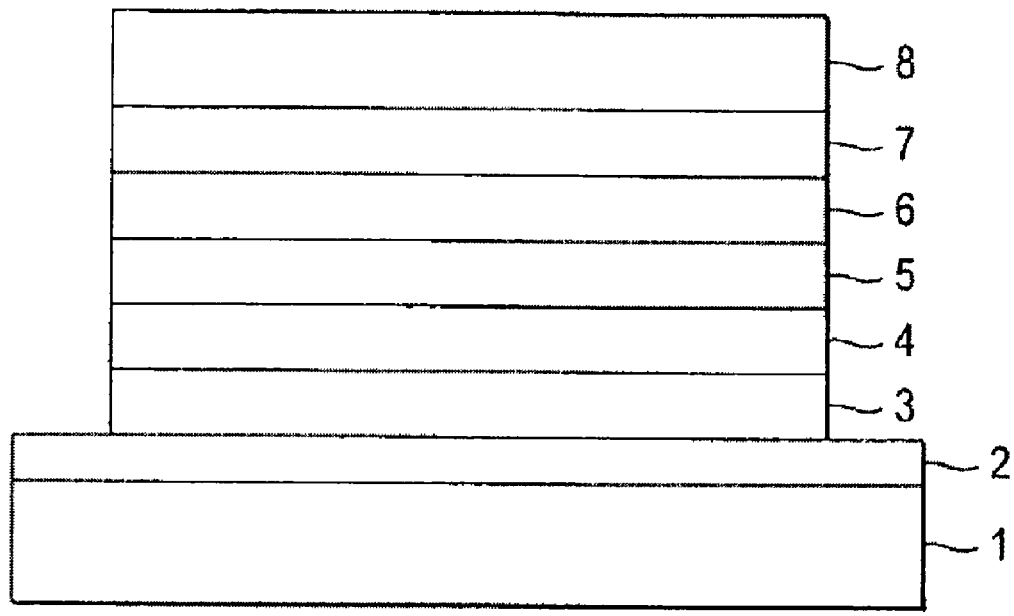
FIG. 3 is a view showing the EL device constitution of Example 6.
Figure 4:
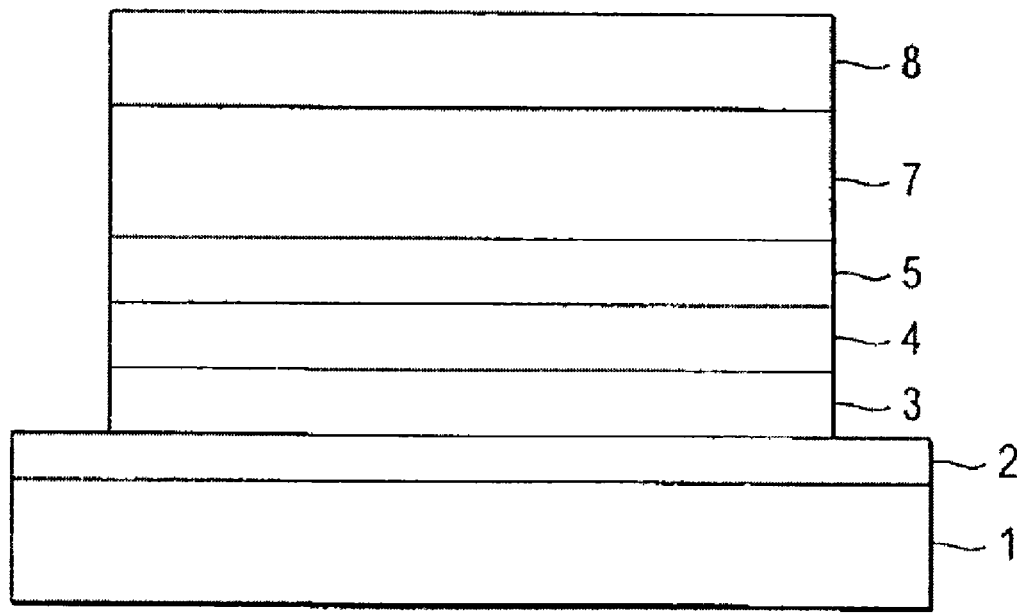
FIG. 4 is a view showing the EL device constitution of Comparative Example 1.
Figure 5:
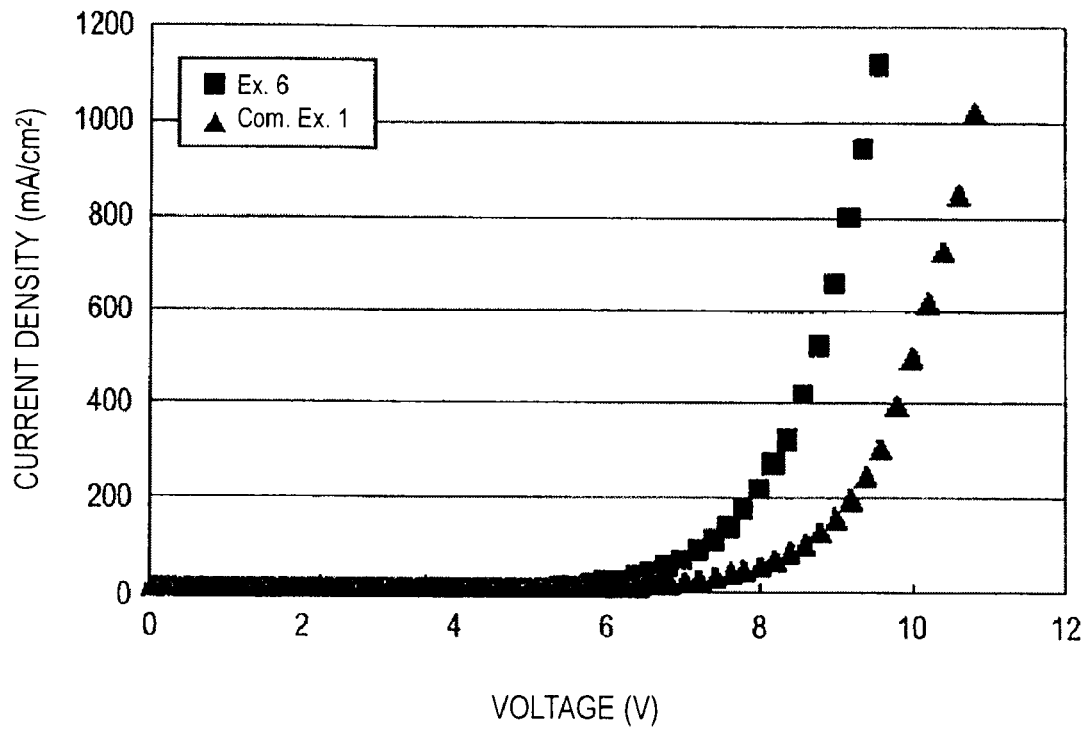
FIG. 5 is a graph comparing voltage/current density characteristics of Example 6 and Comparative Example 1.
Figure 6:
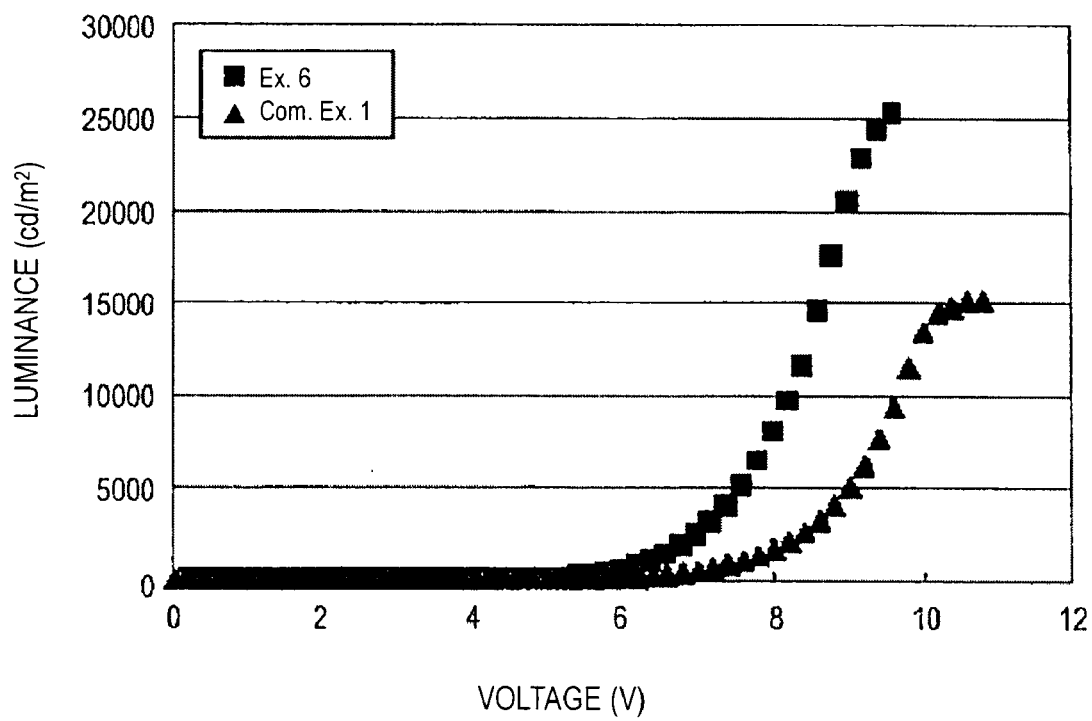
FIG. 6 is a graph comparing voltage/luminance characteristics of Example 6 and Comparative Example 1.
Figure 7:
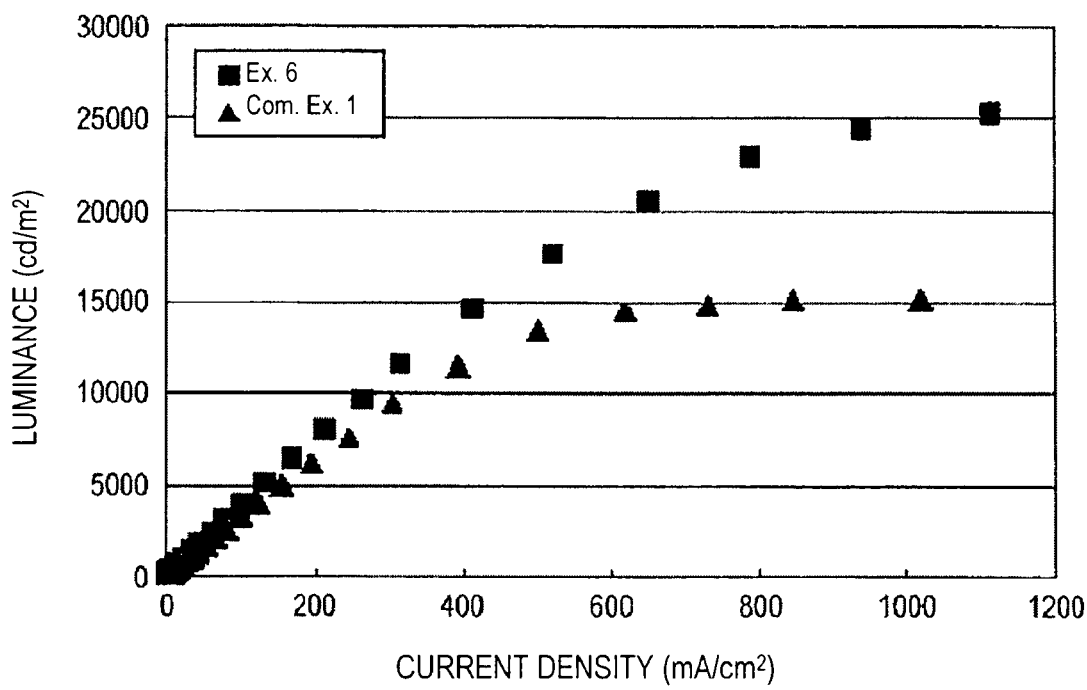
FIG. 7 is a graph comparing current density/luminance characteristics of Example 6 and Comparative Example 1.
Figure 8:
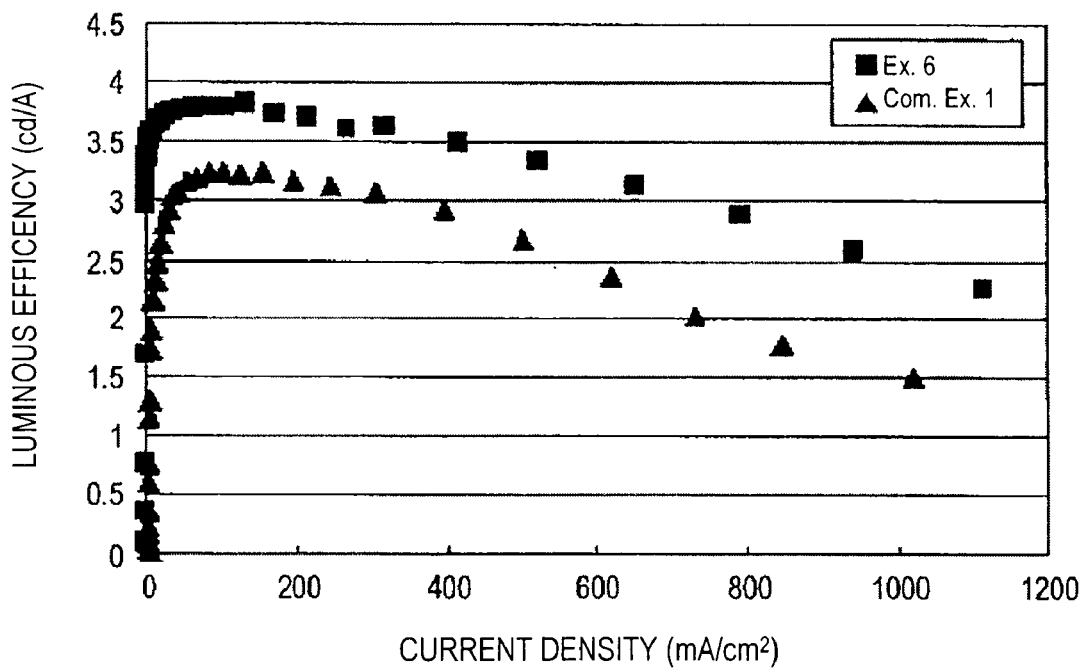
FIG. 8 is a graph comparing current density/current efficiency of Example 6 and Comparative Example 1.

An organic EL device was prepared by vapor-depositing a hole injection layer 3, hole transport layer 4, an emitting layer 5, a hole blocking layer 6, an electron transport layer 7 and a cathode (aluminum-magnesium electrode) 8 in this order on an ITO electrode previously formed on a glass substrate 1 as a transparent anode 2, as shown in FIG. 3.

First, the glass substrate 1 on which an ITO film having a film thickness of 150 nm had been formed was washed with an organic solvent, and then, a surface thereof was washed by UV ozone treatment. This was set in a vacuum vapor deposition apparatus, and the pressure was reduced to 0.001 Pa or less.

Subsequently, CuPc was formed to about 20 nm at a vapor deposition rate of 6 nm/min as the hole injection layer 3. NPD was formed thereon to about 40 nm at a vapor deposition rate of 6 nm/min as the hole transport layer 4. Alq3 was formed thereon to about 30 nm at a vapor deposition rate of 6 nm/min as the emitting layer. On this emitting layer, BpyTHDm (2) of the invention was formed to about 30 nm at a vapor deposition rate of 6 nm/min as a layer serving as both the hole blocking layer 6 and the electron transport layer 7. Finally, the pressure was returned to the atmospheric pressure, and a mask for cathode vapor deposition was inserted. The pressure was reduced again, and an alloy of MgAg was vapor-deposited to about 200 nm at a ratio of 10:1 to form the cathode 8. The device prepared was stored in a vacuum desiccator, and characteristic measurements were performed in the atmosphere at normal temperature.

A DC voltage was applied to the organic EL device of the invention thus prepared. As a result, a light emission of 100 cd/m$^2$ was observed at 5.22 V, and a current of 300 mA/cm$^2$ flowed at 8.35 V to obtain a green light emission of 10870 cd/m$^2$. The luminous efficiency at this luminance was 3.61 cd/A. The maximum luminance of this device before the breakpoint was 25160 cd/m$^2$.

COMPARATIVE EXAMPLE 1

For comparison, an organic EL device was prepared under the same conditions as in Example 6 except that the material for the electron transport layer 7 was replaced by Alq3, and the characteristics thereof were examined. Specifically, Alq3 was formed to about 60 nm at a vapor deposition rate of 6 nm/min as a layer serving as both the emitting layer 5 and the electron transport layer 7. A light emission of 100 cd/m$^2$ was observed at 8.61 V and a current of 300 mA/cm$^2$ flowed at 9.60 V to obtain a green light emission of 9280 cd/m$^2$. The luminous efficiency at this luminance was 3.08 cd/A. The maximum luminance of this device before the breakpoint was 15180 cd/m$^2$.

As shown above, it has been revealed that the organic EL device of the invention is excellent in luminous efficiency compared to the device using Alq3 which has been used as a general electron transport material, further that a significant decrease in driving voltage can be achieved, and furthermore that it is also excellent in heat resistance.

While the invention has been described in detail and with reference to specific embodiments thereof, it will be apparent to one skilled in the art that various changes and modifications can be made therein without departing from the spirit and scope thereof.

This application is based on Japanese Patent Application 2006-082969 filed on Mar. 24, 2006, the contents of which are incorporated herein by reference.

Industrial Applicability

The compound of the invention which has a thiadiazole ring structure substituted with a substituted pyridyl group is good in electron injection, and stable in a thin film state, so that it is excellent as a compound for an organic EL device. The driving voltage can be decreased by preparing the organic EL device using the compound, which can improve durability. For example, development to applications for home electric appliances and illumination has become possible.

The invention claimed is:

1. A compound represented by the following general formula (1), which has a thiadiazole ring structure substituted with a substituted pyridyl group:

[Chem. 1]

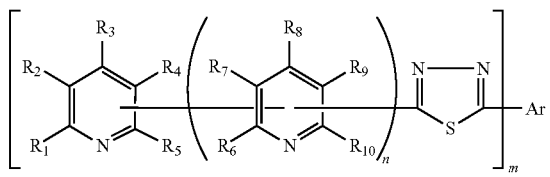

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded and provided that when m=1 R1, R2, R3, R4 and R5, one of which is a linking group and the others of which may be the same of different, each represents a hydrogen atom, a cyano group or a substituted or unsubstituted aromatic hydrocarbon group.

2. A compound represented by the following general formula (1), which has a thiadiazole ring structure substituted with a substituted pyridyl group:

[Chem. 1]

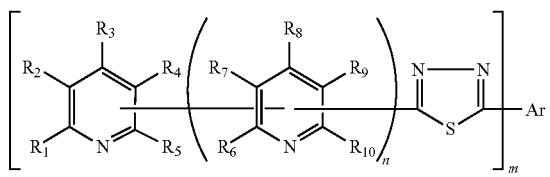

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a fluorine atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded and provided that when m=1 R1, R2, R3, R4 and R5, one of which is a linking group and the others of which may be the same of different, each represents a hydrogen atom, a cyano group or a substituted or unsubstituted aromatic hydrocarbon group, wherein n of said general formula (1) is 1.

3. A compound represented by the following general formula (1), which has a thiadiazole ring structure substituted with a substituted pyridyl group:

[Chem. 1]

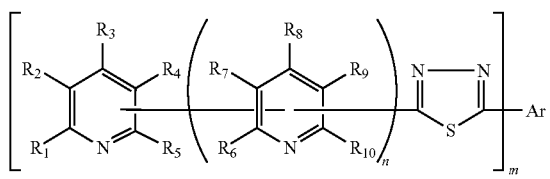

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a fluorine atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded and provided that when m=1 R1, R2, R3, R4 and R5, one of which is a linking group and the others of which may be the same of different, each represents a hydrogen atom, a fluorine atom, a cyano group or a substituted or unsubstituted aromatic hydrocarbon group, wherein n of said general formula (1) is 2.

4. A compound represented by the following general formula (1), which has a thiadiazole ring structure substituted with a substituted pyridyl group:

[Chem. 1]

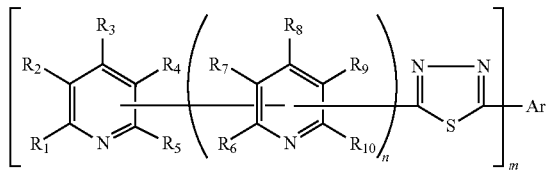

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a fluorine atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded and provided that when m=1 R1, R2, R3, R4 and R5, one of which is a linking group and the others of which may be the same of different, each represents a hydrogen atom, a fluorine atom, a cyano group or a substituted or unsubstituted aromatic hydrocarbon group, wherein n of said general formula (1) is 0, and one of the four groups of R1, R2, R3, R4 and R5 excepting the linking group is a substituted or unsubstituted phenyl group.

5. An organic electroluminescent device comprising a pair of electrodes and at least one organic layer interposed therebetween, wherein at least one organic layer of said organic layer(s) contain, as a constituent material thereof, a compound represented by the following general formula (1), which has a thiadiazole ring structure substituted with a substituted pyridyl group:

[Chem. 2]

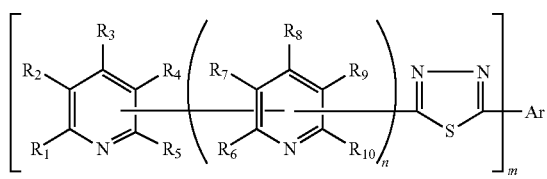

(1)

wherein Ar represents a substituted or unsubstituted aromatic hydrocarbon group, a substituted or unsubstituted aromatic heterocyclic group or a substituted or unsubstituted condensed polycyclic aromatic group; R1, R2, R3, R4 and R5, one of which is a linking group and the others of which may be the same of different, each represents a hydrogen atom, a fluorine atom, a cyano group, an alkyl group or a substituted or unsubstituted aromatic hydrocarbon group; R6, R7, R8, R9 and R10, two of which are linking groups and the others of which may be the same or different, each represents a hydrogen atom, a fluorine atom, a cyano group, an alkyl group or a substituted or unsubstituted aromatic hydrocarbon group; m represents an integer of 1 to 3; and n represents an integer of 0 to 4, provided that when n=0, the case where all the four groups of R1, R2, R3, R4 and R5 excepting the linking group are hydrogen atoms is excluded.

6. The organic electroluminescent device according to claim 5, wherein n of said general formula (1) is 1.

7. The organic electroluminescent device according to claim 5, wherein n of said general formula (1) is 2.

8. The organic electroluminescent device according to claim 5, wherein n of said general formula (1) is 0, and one of the four groups of R1, R2, R3, R4 and R5 excepting the linking group is a substituted or unsubstituted phenyl group.

9. The organic electroluminescent device according to claim 5, wherein said at least one organic layer includes an electron transport layer, and the electron transport layer contains the compound represented by said general formula (1).

10. The organic electroluminescent device according to claim 5, wherein said at least one organic layer includes a hole blocking layer, and the hole blocking layer contains the compound represented by said general formula (1).

11. The organic electroluminescent device according to claim 5, wherein said at least one organic layer includes an emitting layer, and the emitting layer contains the compound represented by said general formula (1).

12. The organic electroluminescent device according to claim 5, wherein said device comprises a structure comprising an anode, a hole injection layer, a hole blocking layer, an electron transport layer and a cathode in this order on a substrate.

13. The organic electroluminescent device according to claim 12, further comprising an electron injection layer between said electron transport layer and said cathode.

14. The organic electroluminescent device according to claim 5, wherein said pair of electrodes comprises an anode comprised of a material selected from the group consisting of ITO and gold.

\* \* \* \* \*